(12) United States Patent
Yaniv

(10) Patent No.: US 6,685,908 B1
(45) Date of Patent: Feb. 3, 2004

(54) PRECIPITATED ARAGONITE AND A PROCESS FOR PRODUCING IT

(75) Inventor: Isaac Yaniv, Haifa (IL)

(73) Assignee: 3P Technologies Ltd., Haifa (IL)

( * ) Notice: Subject to any disclaimer, the term of this patent is extended or adjusted under 35 U.S.C. 154(b) by 0 days.

(21) Appl. No.: 09/519,749

(22) Filed: Mar. 6, 2000

(51) Int. Cl.⁷ .................................................. C01F 11/18
(52) U.S. Cl. ...................................... 423/432; 423/430
(58) Field of Search .............................. 423/432, 430, 423/431, 165, 160

(56) References Cited

U.S. PATENT DOCUMENTS

| | | |
|---|---|---|
| 2,081,112 A | 5/1937 | Statham et al. |
| 2,964,382 A | 12/1960 | Hall, Jr. |
| 3,120,426 A | 2/1964 | Crawford, Jr. |
| 3,320,026 A | 5/1967 | Waldeck |
| 3,669,620 A | 6/1972 | Bennett et al. |
| 4,018,877 A | 4/1977 | Woode |
| 4,157,379 A | 6/1979 | Arika et al. |
| 4,244,933 A | 1/1981 | Shibazaki et al. |
| 4,420,341 A | 12/1983 | Ferrigno |
| 4,427,836 A | 1/1984 | Kowalski et al. |
| 4,469,825 A | 9/1984 | Kowalski et al. |
| 4,824,654 A | 4/1989 | Ota et al. |
| 4,985,064 A | 1/1991 | Redlich et al. |
| 5,043,017 A | 8/1991 | Passaretti |
| 5,164,172 A | 11/1992 | Katayama et al. |
| 5,320,897 A * | 6/1994 | Kondo et al. |
| 5,342,600 A | 8/1994 | Bleakley et al. |
| 5,376,343 A | 12/1994 | Fouche |
| 5,380,361 A | 1/1995 | Gill |
| 5,418,057 A * | 5/1995 | Tokiyoshi et al. |
| 5,593,489 A | 1/1997 | Wu |
| 5,833,747 A | 11/1998 | Bleakley et al. |
| 5,846,382 A | 12/1998 | von Raven |
| 5,846,500 A | 12/1998 | Bunger et al. |
| 5,861,209 A | 1/1999 | Haskins et al. |
| 5,939,036 A | 8/1999 | Porter et al. |
| 6,022,517 A | 2/2000 | Fairchild et al. |
| 6,071,336 A | 6/2000 | Fairchild et al. |
| 6,156,286 A | 12/2000 | Fortier et al. |
| 6,221,146 B1 | 4/2001 | Fortier et al. |

FOREIGN PATENT DOCUMENTS

| | | | |
|---|---|---|---|
| CA | 765756 | 8/1967 | |
| GB | 2145074 | * 3/1985 | |
| GB | 2145074 A | 3/1985 | |
| JP | 59-064527 | * 4/1984 | |
| JP | 59-223225 | * 12/1984 | ............ 423/432 |
| JP | 61-77622 | * 4/1986 | |
| JP | 63-256514 | * 10/1988 | ............ 423/165 |
| JP | 63-260815 | * 10/1988 | ............ 423/165 |
| JP | 2-34514 | * 2/1990 | |
| JP | 4-321515 | * 11/1992 | ............ 423/432 |
| SU | 1558874 | * 4/1990 | |

OTHER PUBLICATIONS

Cole, A., "All right on the white? $TiO_2$ versus alternative white minerals", *Industrial Mineral*, 27–31 (2001).

Stieg, F., "Pigment/Binder Geometry: Interparticulate Relationships", *Pigment Handbook*, 3:203–217 (1973).

First page of U.S. patent 4,244,923, Jan. 13, 1981.*

Industrial Minerals May 2001 Cole All right on the white? $TiO_2$ versus alternative white minerals.

* cited by examiner

*Primary Examiner*—Steven Bos
(74) *Attorney, Agent, or Firm*—Browdy and Neimark, P.L.L.C.

(57) ABSTRACT

Disclosed is a novel form of particulate precipitated aragonite calcium carbonate and a novel process for producing it.

51 Claims, 5 Drawing Sheets

PRECIPITATED ARAGONITE AND A PROCESS FOR PRODUCING IT

FIELD AND BACKGROUND OF THE INVENTION

The present invention relates to a novel form of precipitated aragonite and to a novel process for producing it.

Various routes are known for the production of calcium carbonate, which finds use as a thickening material, as a filler, as an extender, and most of all as a pigment, in a variety of industries such as pharmaceuticals, plastics, adhesives, printing, coating (paint), paper, rubber and in filtration. For such purposes, there may be used ground calcium carbonate (GCC) or precipitated calcium carbonate (PCC). PCC in general possesses advantages over GCC, in that it is economical to produce and its precise composition, or purity, can be more strictly controlled.

The most frequently used chemical process for producing PCC is based on the carbonation of aqueous suspensions of calcium hydroxide (also known as "milk of lime" or "slaked lime") with carbon dioxide gas, or with a carbon dioxide containing gas. This process gives rise to relatively pure precipitated calcium carbonate and is a preferred process, because there are no serious problems of contamination of the product with undesired salts, and moreover it can be controlled in order to adjust the properties of the final product. Thus, the process is based essentially on four stages: firstly, calcination of raw limestone to produce calcium oxide or "quicklime" and carbon dioxide gas or a carbon dioxide containing gas; secondly, "slaking" of the quicklime with water to produce an aqueous suspension of calcium hydroxide; thirdly, carbonation of the calcium hydroxide with carbon dioxide gas or a carbon dioxide containing gas; and finally, downstream operations such as dewatering, drying, deagglomeration, grinding, surface treatment, surface coating, mixing with other minerals (e.g. titanium dioxide, talc, kaolin, GCC, PCC—including aragonite PCC) and dyeing, which allow optimization of the properties of the precipitated calcium carbonate particles in order to be adapted to their intended uses.

Calcium carbonate can be precipitated from aqueous calcium hydroxide slurries or solutions in three different crystallographic forms (polymorphs): the vaterite form which is thermodynamically unstable, the aragonite form which is metastable under normal ambient conditions of temperature and pressure, and the calcite form which is the most stable and the most abundant in nature. These forms of calcium carbonate can be prepared by carbonation of slaked lime by suitable variations of the process conditions.

The calcite form is easy to produce on industrial scales, as precipitated calcium carbonate particles. It exists in several different shapes, of which the most common are the rhombohedral shape and the scalenohedral shape.

Aragonite forms crystals having a length/width ratio (hereinafter—"aspect ratio") in the range between >1:1 and 100:1 of which a typical aspect ratio is 10, in which case the aragonite forms long, thin needles. Therefore, aragonite having a high aspect ratio may be denoted hereinafter—"acicular aragonite" or "needle-shaped aragonite". The production of aragonite is a slow process and is very difficult to control on an industrial scale.

PCC particles are used as thickening materials, fillers, extenders and, most of all, as inexpensive pigments. The latter use implies that a particularly desirable property of this material is its light scattering characteristics, in order to be able impart opacity and brightness to the products containing it. Such characteristics are optimized, when the pigment particles are very effectively dispersed and are apart by an average distance in the range between 0.2 $\mu$m and 0.4 $\mu$m in their final products, and their size distribution is in the range between 0.2 $\mu$m and 0.4 $\mu$m, namely, in the range of half a wavelength of the visible light. That means that either the production of the PCC should be adjusted to produce small particles in order to avoid expensive downstream particle size reduction operations and to cope with the expensive problems of dewatering and drying the product, or, alternatively, the process should be adjusted to produce large particles, and subsequently effect the downstream dewatering and grinding operations. In both cases, the production costs of precipitated calcium carbonate of pigment grades may be doubled or tripled just because of these unavoidable downstream steps.

High light scattering pigments currently available to the above-mentioned industries include titanium dioxide particles, which are very effective to scatter the light due to their relatively high refractive index (2.76; for the rutile form) and their meticulously controlled particle size distribution of which median is in the range between 0.2 $\mu$m and 0.4 $\mu$m. However, this product is of a high specific gravity (~4.0 g/cm$^3$), of a high surface area due to its small particles, and most of all, is quite expensive. Fine kaolin particles are also being used as pigments, but this product has a much lower refractive index (1.56), is of limited whiteness and is still relatively expensive. Particulate calcium carbonate is the ideal least expensive pigment and could replace much more of the titanium dioxide and kaolin pigments in their respective present applications, if it could be prepared in a form having improved light scattering properties.

Calcium carbonate pigments are produced in part by grinding coarse natural rocks and in part by precipitation processes. Of the precipitated calcium carbonate particles, a particulate precipitated aragonite is considered to be the most effective light scattering calcium carbonate pigment, of which refractive indices are 1.530, 1.681 and 1.685, depending on its crystallographic surfaces, its specific gravity is above 2.5 g/cm$^3$, and is the most suitable for same applications. However, its production rate is characteristically very slow and its production conditions are very difficult to control, industrially.

While the majority of references, cited hereinafter, relate to the technology for producing a particulate precipitated aragonite, some of the references are included in order to better present the state of the art for the production of PCC more generally, including the downstream operations, which may be common to all these processes and also to the present invention.

1. U.S. Pat. No. 2,081,112 (N. Statham et al.) describes a process for producing precipitated calcium carbonate by carbonating milk of lime with carbon dioxide containing gas, where the temperature in the gas absorber is maintained at 50–60° C., preferably around 55° C. It is recognized that the more violent the agitation in the gas absorber, the finer will be the product; the aim being to create a fine mist of calcium hydroxide slurry.

2 U.S. Pat. No. 2,964,382 (G. E. Hall, Jr.) describes production of. precipitated calcium carbonate by various chemical routes, in which calcium ions are contacted with carbonate ions in a precipitation zone, the process including also carbonation of milk of lime with carbon dioxide gas. A high shear stator/rotor agitator is used to provide turbulence by rotating at a peripheral speed of at least 1160 feet per minute (589 cm per second) in the precipitation zone. Also, this patent teaches that it is desirable to operate the process at pH values of at least 8.5 and that at temperatures above 60° C., needle-shaped precipitated aragonite particles are formed, which however produce an adverse flow property effect.

3. U.S. Pat. No. 3,320,026 (W. F. Waldeck) describes the production of various forms of precipitated calcium carbonate.

4. GB Patent No. 941,900 (assigned to Kaiser Aluminium & Chemical corporation) describes the production of precipitated aragonite particles, for use as a filter aid, by reacting continuously sodium carbonate solution and aqueous calcium hydroxide slurry at temperatures higher than 60° C. in a multistage system. The product and the solution are withdrawn at the third stage from the bottom of the reactor, the product is then separated from the solution and part of the crystals are recycled to the various stages of the process as seeds for further precipitation of the precipitated aragonite particles.

5. U.S. Pat. No. 3,669,620 (M. C. Bennett et al.) describes a continuous process for the production of a particulate precipitated aragonite by carbonating aqueous calcium hydroxide slurry in sucrose solutions. However, due to the cost of the sucrose, the solution had to be recycled and detrimental materials had to be removed by anion exchange resin. The preferred temperature range was between 60° C. and 90° C.; the pH values were in the range between 7 and 9; and the concentration of the calcium hydroxide was quite low—in the range between one-half and one-twentieth molar.

6. U.S. Pat. No. 4,018,877 (R. D. A. Woode) describes carbonation of calcium hydroxide slurry wherein a complexing agent for $Ca^{++}$ is added to the suspension in the gas absorber, after the calcium carbonate primary nucleation stage and before completion of the carbonation step, the complexing agent being e.g. citric acid, ethylenediamine tetraacetic acid (EDTA), aminotriacetic acid, aminodiacetic acid or a hydroxy polycarboxylic acid. Optionally, long-chain fatty acids or their salts can be added, preferably, after the final carbonation stage.

7. U.S. Pat. No. 4,157,379 (J. Arika et al.) describes the production of a chain-structured precipitated calcium carbonate by the carbonation of calcium hydroxide suspended in water in the presence of chelating agents, such as aliphatic carboxylic acids, and water-soluble metal salts.

8. U.S. Pat. No. 4,244,933 (H. Shibazaki et al.) describes a multi-stage production process for producing a particulate precipitated aragonite, using aqueous calcium hydroxide slurry and carbon dioxide gas or a carbon dioxide containing gas, in the presence of phosphoric acids and water-soluble salts thereof.

9. U.S. Pat. No. 4,420,341(T. H. Feringo) describes inorganic fillers (including calcium carbonate) surface modified with carboxylic acids, antioxidants and high-boiling non-reactive liquid agents.

10. JP Patent Publication No. 63260815 (H. Shibata et al.) describes the production of a particulate precipitated aragonite, by reacting carbon dioxide gas with an aqueous calcium hydroxide slurry in presence of phosphoric acid, a phosphoric acid compound, a barium compound and a strontium compound.

11. JP Patent No. 1261225 (H. Shibata et al.) describes reacting carbon dioxide gas with an aqueous calcium hydroxide slurry, in order to produce a particulate precipitated aragonite, which is stated to have improved properties compared with particulate precipitated calcite.

12. U.S. Pat. No. 4,824,654 (Y. Ota et al.) describes a process for producing precipitated needle-shaped (5–100 $\mu$m) particulate precipitated aragonite, in which a relatively dilute aqueous calcium hydroxide solution (0.04–0.17 wt. %) and carbon dioxide gas or a carbon dioxide-containing gas are reacted together at a temperature of not less than 60° C., in a continuous or semi-continuous (intermittent) manner. [That can be said about the entire relevant prior art]

13. U.S. Pat. No. 5,043,017 (J. D. Passaratti) describes a process for producing acid-stabilized precipitated calcium carbonate particles.

14. U.S. Pat. No. 5,164,172 (H. Katayama et al.) describes a process for producing a particulate precipitated aragonite, in which a mixture of aqueous calcium hydroxide slurry, aragonite calcium carbonate particles and a water-soluble phosphoric acid compound are premixed prior to the addition of carbon dioxide gas.

15. U.S. Pat. No. 5,342,600 (I. S. Bleakley et al.) describe a process of producing particulate precipitated calcium carbonate, in which aqueous calcium hydroxide slurries of varying concentrations are reacted with carbon dioxide-containing gas under a controlled mixing speed. It is recommended therein to prepare the aqueous calcium hydroxide suspension under high shear mixing and subsequently to lower the energy and shear agitation in the reaction mixture in which the precipitated calcium carbonate particles are formed.

16. U.S. Pat. No. 5,376,343 (P. M. Fouche) describes a process for producing various forms of particulate PCC. In the case of aragonite, a mixture of quite dilute aqueous calcium hydroxide solution and a water-soluble source of specific anions (e.g. ammonium nitrate) are premixed prior to addition of $CO_2$ gas.

17. U.S. Pat. No. 5,380,361 (R. A. Gill) describes inter alia calcium carbonate particles coated with C12–C22 fatty acids salts.

18. U.S. Pat. No. 5,593,489 (K-T. Wu) describes a process for producing acid-resistant calcium carbonate particles for making neutral to weakly acid paper.

19. U.S. Pat. No. 5,833,747 (I. S. Bleakley et al.) describes a process for producing a particulate precipitated aragonite, in which an aqueous calcium hydroxide slurry (148 g $Ca(OH)_2$ per liter of suspension) is reacted with carbon dioxide gas at an exceptionally slow rate of 0.0026 moles per minute per mole of $Ca(OH)_2$ in a batch operation.

20. WO 9852870 (B. Jackson et al.) describes a multi-stage commercial process for producing a particulate precipitated aragonite, using coarse-grained precipitated aragonite particles as a seeding material. Though the process is claimed to be industrially applicable, it is quite slow and thus of very limited economical value.

21. U.S. Pat. No. 5,846,500 (J. W. Bunger et al.) describes a process for producing a particulate precipitated aragonite, in which an aqueous calcium hydroxide solution is reacted with $CO_2$ gas in a plug-flow reaction system.

22. U.S. Pat. No. 5,846,382 (A. von Raven) describes a process for producing inorganic fillers and pigments, including particulate calcium carbonate, of improved whiteness, brightness and chromaticity.

23. U.S. Pat. No. 5,861,209 (W. J. Haskins et al.) describes a process for producing a particulate precipitated aragonite, for printing, in which an aqueous calcium hydroxide slurry is first mixed with precipitated aragonite particles for seeding and then it is reacted quite slowly with carbon dioxide gas in a batch operation. After dewatering the product to a cake containing about 70% solids, it is mixed with a typical dispersant, e.g. sodium polyacrylate, and it is further dispersed. This patent discloses the use of mixtures of a particulate precipitated aragonite, with $TiO_2$ and other inorganic fillers, pigments and flame retardants.

24. U.S. Pat. No. 5,939,036 (A. L. Porter et al.) describes a process for producing a particulate precipitated aragonite, in which aqueous mixtures of organic compounds and acids (e.g. ethanclamine and HCl) are used to dissolve impure CaO and to form a calcium hydroxide mixture, which is then reacted with carbon dioxide gas to yield various forms of PCC, depending on the temperature. Controlling the temperature of the carbonation at about 95° C. leads to aragonite.

25. U.S. Pat. No. 6,022,517 (G. H. Fairchild et al.) describes a process for producing mixtures of precipitated acicular calcite and acicular aragonite particles in the ratio of 75:25 to 25:75, by reacting carbon dioxide gas or a carbon dioxide containing gas and aqueous calcium hydroxide in the presence of a water soluble aluminum compound, by controlling the specific conductivity in a range >4.0 and up to about 7.0, milliSiemens/cm, at a reaction temperature of from 25–60° C.

26. Pigment Handbook (Vol. I–III; Edited by T. C. Patton; John Wiley & Sons, New York (1973)) describes the properties, the production processes and various uses of aragonite calcium carbonate pigment (c.f. Vol. I; Pages 119–128), as well as those of other pigments that compete in the same market like titanium dioxide, kaolin, GCC, etc. The discussion concerning the influence of the film porosity on the hiding power or opacity of a coating film (c. f. Vol. III; Pages 203–217 and especially on Page 212) may help in understanding some aspects of the present invention.

The entire contents of the above-cited literature, including patents and patent publications, are incorporated herein by reference. It is apparent from the state of the art that known processes for the industrial production of substantially pure particulate precipitated aragonite (>90 parts aragonite: <10 parts calcite), by reacting aqueous calcium hydroxide slurries with carbon dioxide gas or a carbon dioxide containing gas, exhibit serious drawbacks that affect the quality and cost of the final product, as follows:

A. Some of the processes are conducted in aqueous solutions of extremely low concentrations of calcium hydroxide. In some cases it is specified that clear solutions, which contain less than 1 wt. % calcium hydroxide, should be used.

B. In those processes which allow use of aqueous calcium hydroxide slurries, the production rates are very slow and difficult to control.

C. To increase somewhat the rates of production in processes of A and B, the prior art recommends seeding with previously produced aragonite particles. However, this complicates the production processes, especially those operated continuously, and which are otherwise of great commercial potential.

D. Dewatering of particulate precipitated aragonite obtained according to the known art gives rise to relatively wet filter cakes of which the water content is not below 30% and which may thus require a very expensive subsequent drying step.

E. Particulate precipitated aragonite of the prior art requires extensive grinding operations to optimize its particle size distribution (PSD) in order to meet the effective PSD in the range between 0.2 µm and 0.4 µm, mentioned above. Moreover, the grinding operation tends to contaminate the product, due to attrition of the grinding media, unless very expensive materials of construction are used for this purpose.

F. The known particulate precipitated aragonite is of limited whiteness, mainly due to the high residual impurities in the $CaCO_3/CaO$ feedstock, which it is quite difficult to remove thoroughly, on the industrial scale. Also, the low whiteness of the product is a limiting factor in choosing the suitable sources of its raw materials ($CaCO_3/CaO$).

G. Particulate precipitated aragonite frequently requires one or more post-manufacturing treatment step(s), in order to ensure that the particle surface is hydrophobic, by coating with suitable long-chain carboxylic acids and/or other materials such as silicon greases, e.g. for efficient dispersal in hydrophobic media such as rubber or plastics, and/or to ensure resistance to acidic environments for use e.g. in the paper industry and in the coating industry.

H. Efforts in the prior art to increase the effective refractive index of particulate precipitated aragonite has not so far succeeded in making this material a serious competitor to titanium dioxide.

Accordingly, it is an object of the present invention to overcome all or most of the problems encountered in:the prior art, as mentioned in paragraphs A–H, above.

It is an object of the present invention to provide particulate precipitated aragonite, as stated in the preceding paragraph, by a process which is more efficient and less expensive, than those available in the prior art.

It is yet a further object of the present invention to effect such a more efficient and less expensive process as stated in the preceding paragraph, using sources of $CaCO_3/CaO$, which are presently not suitable raw materials for use as e.g. fillers, extenders and pigments, and for other applications, in all of which uses require pigments of high optical properties and high performance, whereby production costs are lowered.

Still another object of the present invention is to provide a particulate precipitated aragonite of a superior quality as stated above, in which the produced particles are treated in situ with a hydrophobic agent in order to avoid an extra downstream step and to fine-tune their properties to meet the requirements of the rubber, plastics, coatings (especially durable paints in acidic environments), inks and paper industries (especially paper production in weakly acidic media), an effect of said in situ treatment being lowering of production costs.

Still another object of the present invention is to carry out the above-stated more efficient and less expensive process, in a manner which gives rise to filter cakes which are relatively dry, e.g. with no more than about 20 wt. % water, right after the dewatering stage, and thus additionally lowering production costs.

Another object of the invention is to effect the above-stated more efficient and less expensive process, in such a manner that the produced particulate precipitated aragonite does not require, for most applications, any downstream grinding operations, except for the regular mixing systems which are in any event usually installed in the industries mentioned above, and thus additionally lowering production costs.

Most of all, it is a particular object of the present invention to provide a particulate precipitated aragonite of a better quality than that obtained in the prior art, and especially having a higher whiteness, a lower specific gravity and a higher effective refractive index.

Other objects of the invention will appear from the description which follows.

SUMMARY OF THE INVENTION

It has been surprisingly found in accordance with the present invention, that an industrially viable particulate precipitated aragonite calcium carbonate, which is characterized by its high whiteness, high effective refractive index, and especially by its low specific gravity (below 2.5 g/cm$^3$), can be produced, and that the above-mentioned objects of the present invention can be achieved, by a process which comprises reacting an aqueous calcium hydroxide slurry with a gas selected from carbon dioxide and a gas containing it, wherein the parameters of the process, including e.g. at least one preselected active agent, modes of operation, operating concentrations of raw materials, operating temperatures, operating pH range and high shear mixing speeds are strictly controlled such that the desired product is obtained. In a particular embodiment, flotation of the product occurs during such process The process of the invention for producing a particulate precipitated aragonite in accordance with the invention, is preferably further characterized by at least one, and preferably all, of the following features: (a) the active agent comprises at least one member selected from the group consisting of carboxylic acids of formula $CH_3(CH_2)_n COOH$, where n is 7–9, and their carboxylate salts, esters, anhydrides, and acyl halides, and ketenes of formula $CH_3(CH_2)_{n-1}C=C=O$; (b) the concentration of the active agent is within the range of between 0.2 wt. % and 10 wt. %, calculated as $CH_3(CH_2)_n COOH$ and based on the weight of calcium carbonate, (c) the slurry contains calcium hydroxide in a concentration within the range of from 3 to 30 wt. %, more preferably 4 to 20 wt. %; (d) the product is produced at a pH between 8 and 11, preferably between 9 and 10; (e) the process is effected at a temperature in the range between 60° C., desirably between 80° C., and the boiling temperature of the reaction mixture; (f) the process is effected either in a semi-continuous (intermittent) mode of operation, or more preferably in a continuous manner; (g) the process is effected under high shear mixing e.g. with a mixer comprising a rotor/stator or a rotor only, the mixer peripheral (tip) speed being preferably at least 5 m/sec. In a particular embodiment, this process is effected in a continuous mode of operation under high shear mixing with a mixer comprising a rotor/stator or a rotor only, at a temperature in the range between 90° C. and the boiling temperature of the reaction mixture, the active agent—preferably present in an amount in the range between 0.2% and 10 wt. %, calculated on the weight Of calcium carbonate—being selected from the Carboxylic acids and their calcium salts, and the slurry contains calcium hydroxide in a concentration within the range of from 5 to 15 wt. %, the active agent being desirably premixed with the calcium hydroxide slurry prior to reaction with carbon dioxide. The present invention also provides as a novel chemical substance—which is of course obtainable in accordance with the present process, a particulate precipitated aragonite, which has a specific gravity of <2.5 g/cm$^3$ (preferably <2.3 g/cm$^3$, more preferably <2.0 g/cm$^3$, even more preferably <1.8 g/cm$^3$) after drying at 120° C., and a specific gravity <2.5 g/cm$^3$ after ignition for eight hours at 500° C. In a particular embodiment, the product has a specific gravity of <2.3 g/cm$^3$ after drying at 120° C., and a specific gravity <2.3 g/cm$^3$ after ignition for eight hours at 500° C.

A typical such product may be further characterized by at least one of the following features; it contains said carboxylate calcium salt(s) in an amount between 0.2 and 10 wt. %, calculated as $CH_3(CH_2)_n COOH$ and based on the weight of calcium carbonate; it has a specific gravity <2.2 g/cm$^3$, preferably <2.0 g/cm$^3$, more preferably <1.8 g/cm$^3$; a product previously dried at 120° C. for 12 hours has a loss on drying at 300° C. for 8 hours of <10% wt %, based on the weight of calcium carbonate; a product previously dried at 120° C. for 12 hours has a loss on ignition at 500° C. for 8 hours of <10% wt. %, based on the weight of calcium carbonate; after drying at 120° C. for 12 hours, and/or drying for 8 hours at 300° C., and/or firing for 8 hours at 500° C., it still has a specific gravity <2.5 g/cm$^3$.

The product of the present invention can be used as a thickening material, a filler, an extender and particularly as a pigment for the pharmaceuticals, plastics, adhesives, printing, coating (paint), paper, rubber, filtration, and many other industries.

DETAILED DESCRIPTION OF THE INVENTION

In the process of the present invention, a slurry of calcium hydroxide in water and carbon dioxide gas or a carbon dioxide containing gas are reacted together in the presence of the active agent under stringent process conditions, to generate a particulate precipitated aragonite having unique properties.

The product of the present invention is characterized by its low production cost and by its unique physical properties (high whiteness, high effective refractive index and low specific gravity (<2.5 g/cm$^3$)) and by its excellent chemical properties (hydrophobicity and resistance to weak acids), which make it particularly suitable as a thickening material, a filler, an extender and most of all as a pigment for the printing, coating (paint), paper, rubber, plastics, filtration, adhesives, pharmaceuticals and other industries.

Figure 1:
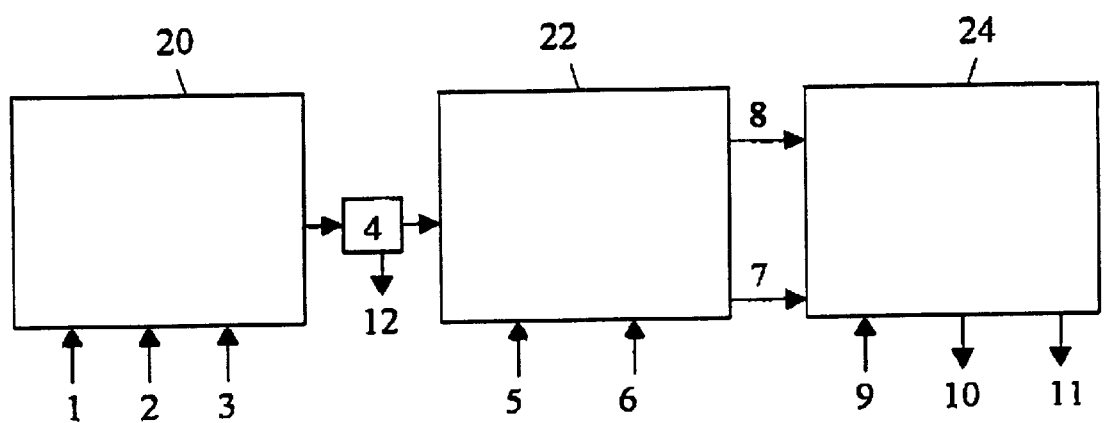
FIG. 1 shows a schematic flow sheet for production of particulate precipitated calcium carbonate according to the prior art.
Figure 2:
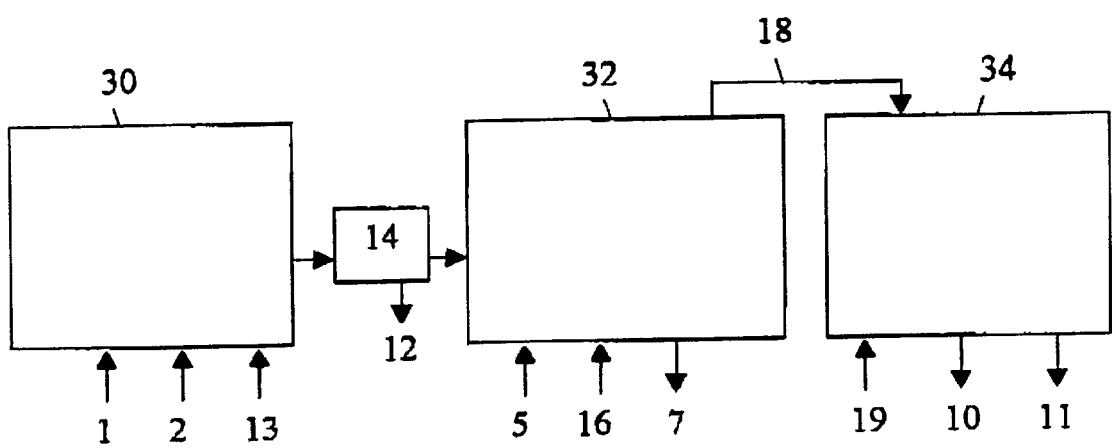
FIG. 2 shows a schematic flow sheet for production of a particulate precipitated aragonite, in accordance with an embodiment of the present invention.
Figure 3:
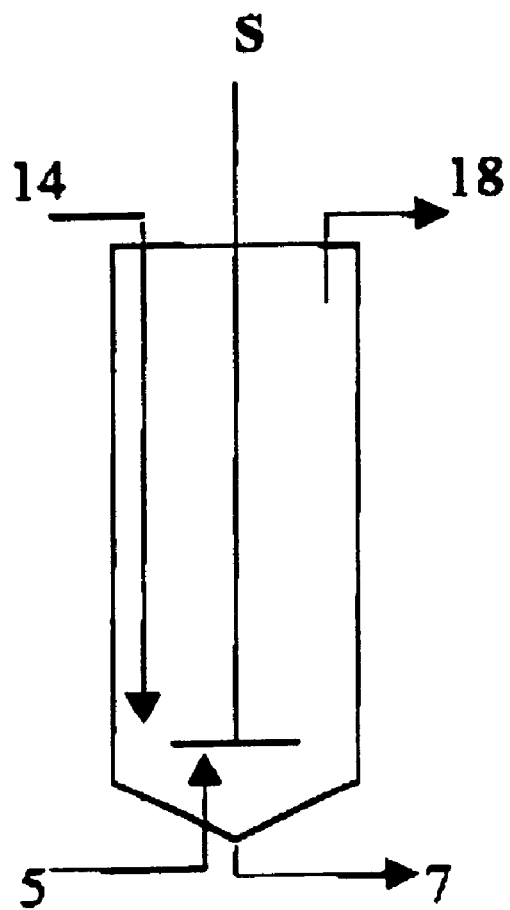
FIG. 3 shows in schematic vertical section, a reactor/flotation cell for producing a particulate precipitated aragonite, in accordance with an embodiment of the present invention.

As stated above, FIG. 1 shows a flow sheet for production of particulate precipitated calcium carbonate according to the prior art. By contrast, in order to define the most suitable conditions to operate the carbonation stage of the present invention, a detailed description of parameters for the present process is given below. These also include some details of how to operate the upstream and downstream stages of the carbonation stage, as these may affect the final outcome (c. f. FIGS. 2 and 3).

In FIG. 1, which is a schematic representation of a prior art procedure for making a precipitated calcium carbonate, quicklime (CaO) and water which react together giving slaked lime are fed to reactor 20 via respective conduits 1 and 2, and optional additives such as aragonite calcium carbonate particles for seeding, phosphoric acids and salts, chelating agents, dispersants, and surface active agents, may also be added at this stage via conduit 3. The initial product "milk of lime" (calcium hydroxide) is fed via filter or hydrocyclone 4 (large solid particles being removed at 12) into carbonator 22, to which there is also fed gaseous carbon dioxide (or a gas containing it) via conduit 5 and the aforementioned optional additives via conduit 6. The reaction product including any contaminants exits carbonator 22 as an underflow via conduit 7 and/or an overflow via conduit 8, to further operations (at site 24) such as dewatering, grinding and coating; for such further operations there may be added optionally via conduit 9, e.g. dispersants, surface active agents, greases, silicon greases, long-chain carboxylic acids and their salts, inorganic pigments, and/or dyeing agents. The filtrate and water vapors exit the system via conduit(s) 10, while the final product (which may be wet or dry and optionally post-treated) exits via conduit 11.

In FIG. 2, which is a schematic representation of a procedure for making a particulate precipitated aragonite in accordance with the present invention, quicklime (CaO) and water which react together giving slaked lime are fed to reactor 30 via respective conduits 1 and 2, and the present active agent (and optionally also additives such as phosphoric acids and salts, chelating agents, dispersants, and surface active agents) may be added at this stage via conduit 13. The initial product "milk of lime" (calcium hydroxide) together with active agent if added to 30 (and optional additives) is fed via filter or hydrocyclone 14 (large solid particles being removed at 12) into carbonator 32, to which there is also fed gaseous carbon dioxide (or a gas containing it) via conduit 5 and the active agent (and possibly the aforementioned optional additives) via conduit 16. It will be appreciated that the active agent may be added either to reactor 30 or to carbonator 32, or to both. Contaminants and liquid exit carbonator 32 as an underflow via conduit 7, whereas— owing to the fact that an embodiment of the present process includes simultaneous flotation—the desired product exits as an overflow via conduit 18, to further operations (at site 34) such as dewatering, grinding and coating; for such further operations there may be added optionally via conduit 19, e.g. dispersants, surface active agents, greases, silicon greases, long-chain carboxylic acids and their salts (including if desired those within the definition of the present active agents), inorganic pigments, and/or dyeing agents. The filtrate and water vapors exit the system via conduit(s) 10, while the final product (which may be wet or dry and optionally post-treated) exits via conduit 11.

Slaking of Quicklime

Though this operation is well known in the prior art, it is worthwhile to choose a preferred mode of operation which is best adapted to the process of the present invention. Thus, fresh slaked lime is preferably prepared in a continuous mode of operation, which enables operation of the downstream carbonation stage using low inventories and exploiting to its maximum the energy that is liberated in the reaction between the water and the CaO, before this precious energy is lost to the surroundings. The present invention desirably makes use of this energy to effect the step of carbonation of the aqueous calcium hydroxide slurry at relatively high temperatures, more preferably without cooling or heating, or in other words, without adding or subtracting energy, and thus utilizing only the energy liberated by the cabonation reaction together with the energy produced by a powerful mixing system. Once again, use of fresh and still warm milk of lime is preferably an important factor in the success of the carbonation stage and this is more preferably effected, as mentioned above, in a continuous mode of operation, the temperature of the slaked lime being preferably maintained at somewhat below the temperature of the carbonation stage. However, in the alternative, a batch mode of operation may also be used for process of the present invention.

Mixing of Quicklime

In some prior art patents it is recommended to use high shear mixers to slake the CaO with water. The process of the present invention is quite tolerant to the kind of mixing, as long as the slaking reaction is complete and the maximum energy is liberated. Mixers that comprise rotor/stator mixing systems and mixers that comprise rotors only are suitable.

Purification of Slaked Lime Prior to Carbonation

There are numerous methods of purifying slaked lime before its utilization in the carbonation stage. Filters to remove large insoluble particles and/or separation of these particles by hydrocyclones are two efficient methods for this purpose. Usually, particles of greater diameter than 40 μm (up to 70 μm) are removed prior to the carbonation stage and the coarse particles can then be discarded or used in the construction industry, for example. The fine slurry is then ready for carbonation in the subsequent downstream stage.

Sources of $CaCO_3/CaO$

Many sources of $CaCO_3/CaO$ are too contaminated to be used to produce by known methods, a particulate precipitated aragonite for the printing, coating (paint), paper, rubber, plastics, filtration, glue, pharmacy and other industries and their main use is, as very inexpensive materials, in the construction industry. On the other hand, the present invention may allow utilizing many of these "impure" $CaCO_3/CaO$ sources and turning them into a particulate precipitated aragonite, of filler, extender and pigment grades. The present invention, as is manifested in the carbonation stage, is superior over any state of the art technology in salvaging $CaCO_3$ mines and turning them to profitable use, without changing greatly the state of the art methods for preparing the slaked lime.

Use of Additives

The state of the art technology for slaking quicklime includes adding a variety of additives into the milk of lime prior to the carbonation stage. According to the present invention, one of the preferred modes of operation is to add the active agent into the milk of lime prior to the carbonation reaction. Those skilled in the art of producing precipitated calcium carbonate must carefully check that the other additives, if any are present in the milk of lime, do not interfere with the ability of the active agent to enhance formation of particulate precipitated aragonite and to cause its flotation in the carbonation reactor. For instance, the use of 1 wt. % (based on the calcium carbonate) of phthalic acid or trimelitic acid with about 1 wt. % (based on the calcium carbonate) of the active agent, cause the formation of particulate calcite in the carbonation stage, instead of aragonite. In other cases, the additives may cause the formation of mixtures of particulate precipitated calcite and aragonite.

The Reaction/Carbonation Stage

This operation is well known in the prior art. However, as this stage is the essence of the present invention, it is worthwhile to choose the mode of operation that suits it best. For example, although the use of aragonite particles for seeding is a recommended procedure in the prior art, it seems at the present time that this practice is unlikely to have any particular utility in the process of the present invention, since use of the active agent enables all desired objectives to be achieved.

As the most important functions of the active agent in the present invention are to catalyze the production of particulate precipitated aragonite, to cause its flotation in the carbonation reactor and to improve the physical and chemical properties of the resulting product, all necessary measures should be taken in order to maximize these functions.

The Nature of the Active Agent and Its Origin

While the scope of the present invention is not to be regarded as limited by any theory, nevertheless it may be likely that the calcium salts of the carboxylic acids of the general formula: $CH_3(CH_2)_nCOOH$, where n=7, 8, and 9 (or mixtures thereof), operate in practice as the functioning active agent in the present process. It should not be ruled out, however, that for example, other derivatives of such acids within the scope of the invention may participate in similar activity.

The above-mentioned calcium salts of the relevant acids may be used as raw materials in the present invention. However, other compounds, which undergo chemical transformations to form the active agent under the process conditions, also serve this purpose as raw materials in the production of the desired particulate precipitated aragonite.

In a particular embodiment of the invention, the active agent is selected from carboxylic acids of the general formula: $CH_3(CH_2)_nCOOH$, where n=7, 8, or 9, and including mixtures thereof. All three acids can be quite easily introduced into any of the production facilities. Pumping of these acids when their temperature is held above their melting points (e.g. >60° C.) seems to be a very useful method to deliver the acids into the suitable production units. Under such conditions, these thermally stable acids are immediately converted into their respective calcium salts when they are mixed with the hot aqueous calcium hydroxide slurry or with the hot carbonation mixture at pH>7. As water is the only by-product of the reaction between the calcium hydroxide and the respective acids, the use of these acids, as raw materials in the process of the present invention, seems to have no harmful side effect.

The respective acid anhydrides of the general formula: $(CH_3(CH_2)_nCO)_2O$, including mixtures thereof, where n=7, 8, and 9, are as good a source for the active agent, as the corresponding acids. However, the anhydrides are much less safe to handle and they are much more expensive than the respective acids.

The carboxylate salts of the acids of the general formula: $CH_3(CH_2)_nCOOH$, including mixtures thereof, where n=7, 8, and 9, can serve as raw materials in the process of the present invention, e.g. where the cations are selected from $Na^+$, $K^+$, $NH_4^+$, Li+, $Mg^{++}$ and especially $Ca^{30\,+}$, but, generally, the use of these salts does not appear to have any advantage over the free acids. On the contrary, the salts are more expensive, they are not as easy to handle on an industrial scale as the respective acids and, except the $Ca^{++}$ salts, all the other salts add cations that, so far as is presently known, are not required in the present process. The $Mg^{++}$ salts present a special case, as they leads to the formation of hydromagnesite and thereby to a dramatic rise of the surface area of the product, to its contamination and to a large increase in the water content in the wet filter cake. Therefore, in the process of the present invention only limited concentrations of this cation are desired, i.e. <3 wt. %, based on the calcium hydroxide.

Esters of the following general formula: $CH_3(CH_2)_n$ COOR, where n=7, 8, and 9 and R is an esterification radical such as alkyl, e.g. $CH_3$, $C_2H_5$, $C_3H_7$, etc., are also suitable candidates for the active agent in the present invention. However, in order for these compounds to generate e.g. the corresponding calcium salts, they have to undergo a basic hydrolysis, which may preferably be done by premixing them in the hot and basic aqueous calcium hydroxide slurry, in which they are hydrolyzed and thus converted to the respective $Ca^{++}$ salts. However, the use of these esters in the process of the invention appears to be inferior to the use of the respective acids, for reasons which will be self-evident to the skilled person.

Chemically equivalent to the other preferred active agents specifically mentioned above, are ketenes of the general formula: $CH_3(CH_2)_{n-1}C{=}C{=}O$, wherein n=7, 8, and 9, and including mixtures thereof, behave in a similar manner and entail similar drawbacks, as for the acid anhydrides, as mentioned above.

Therefore, the acids of the general formula: $CH_3(CH_2)_n$ COOH, wherein n=7, 8, and 9, including mixtures thereof, are the presently preferred source for the active agent to be used in the process of the present invention. More specifically, decanoic acid (wherein n=8) is the presently preferred acid, since it is the least expensive in this series of active carboxylic acids and it is located at the middle of the range of these active acids having n=7, 8 and 9.

The Reactor/Carbonator/Flotation Cell

As already mentioned above, the carbonation stage can be conducted in any well-stirred reactor according to the prior art. However, due to the fact that the active agent is a unique material that can enhance the formation of particulate precipitated aragonite, in the reaction between aqueous calcium hydroxide slurries and carbon dioxide gas or a carbon dioxide containing gas, and also due to the fact that the active agent can cause this product to float, the presently preferred carbonators to be used in the process of the present invention are flotation cells.

These cells may be operated somewhat differently from the regular carbonators and the regular flotation cells, as both functions (carbonation and flotation) take place in the same production unit for particulate precipitated aragonite of the present invention. The exact set-up of these flotation cells can vary, as this will depend on, for example, the preferences of the skilled designer, the precise nature of the desired product, the quality of the aqueous calcium hydroxide slurries, etc. For example, a flotation cell like that depicted in FIG. 3, containing stator/rotor or rotor only S, is suitable for carrying out the inventive process, and of which the main features are as follows:

A. The stream of slaked lime (14) is preferably introduced near the inner circumference of the reactor and above the stirring blades.

B. The stream (5) of carbon dioxide gas or carbon dioxide containing gas is preferably introduced through suitable spargers at a point below the stirring blades, but still not too close to the bottom of the cell, to avoid excessive mixing near the outlet stream (7) of the contaminants and liquid.

C. The wet product and the gas are preferably discharged from the top (18) of the cell. The customary skimmer for skimming the product out of the flotation cell, and hydrocyclones for efficient product/gas separation, are not shown in FIG. 3.

Mode of Operation in the Carbonation Step

Continuous reaction/carbonation of the aqueous calcium hydroxide slurry with carbon dioxide gas or a carbon dioxide containing gas is the most suitable mode of operation for the present invention, especially because of the huge potential market for the produced particulate precipitated aragonite.

Semi-continuous (intermittent) operations may also be used. However, as may be understood from the desirability of operating the process at its utmost efficiency, e.g. as a flotation operation, it is unlikely that an intermittent mode of operation can compete economically with the continuous mode of operation.

A "real" batch mode of operation, in which the milk of lime and the active agent are mixed together and carbon dioxide gas or a carbon dioxide containing gas is introduced to precipitate the desired product until the reaction mixture turns neutral (at about pH~7), appears not to be viable, probably because the active agent is not efficient in catalyzing the formation of particulate precipitated aragonite, at the high initial pH characteristic of the batch mode of operation in this case, and/or because the active agent is adsorbed onto the surface of the first formed crystals of particulate precipitated aragonite, where it is then "buried" under the subsequent precipitated calcium carbonate. In such circumstances, the active agent is very quickly depleted from the reaction mixture, and the process of the invention, as such, is likely to become inoperable.

Temperature of the Carbonation Step

The prior art teaches producing a particulate precipitated aragonite, at a temperature range between 60° C. and the boiling temperature of the reaction mixture, at ambient pressure, and the present process is preferably conducted similarly, because lower temperatures favor the formation of calcite.

On the other hand, operating the process at a temperature as close as possible to the boiling point of the reaction mixture is presently particularly preferred, since these conditions give a product of relatively lower water content in the wet filter cake, which is a great advantage in many applications of the product. While the present process may be operated at higher temperatures and pressures (since the active agent is stable under such conditions), this kind of operation is associated with serious technological problems that may adversely affect the whole economics of the process.

Concentration of Ca(OH)$_2$ Slurry in the Carbonation Step

The prior art method for producing a particulate precipitated aragonite, may be classified into three principle modes of operation. The first mode is operated at very low concentrations of the calcium hydroxide in water, and in some cases a clear solution of <1 wt. % calcium hydroxide is used. In the second mode, there are used aqueous calcium hydroxide slurries and active agents to induce the formation of the desired particulate precipitated aragonite, albeit, at very low production rates. In the third mode particulate precipitated aragonite is used for seeding, in order to improve production rates.

The present invention requires relatively high concentrations in the aqueous calcium hydroxide slurries and the production rates are very fast. Actually, at the range of very low concentrations of <3 wt. % (based on the calcium hydroxide) the present process may not "ignite" right away and under these circumstances, only precipitated calcite calcium carbonate particles may be obtained.

The present invention can use quite dense aqueous calcium hydroxide slurries of up to about 30 wt. % calcium hydroxide, but such dense slurries are very viscous and are very difficult to handle. Therefore, the preferred range of concentrations of the aqueous calcium hydroxide slurries, according to the present invention, are in the range between 4% and 20 wt. %, and more preferably between 5% and 15 wt. % calcium hydroxide. In these ranges, the viscosity of the reaction mixture permits smooth operation, while the energy maintained already in the feed of aqueous calcium hydroxide slurry (as discussed above), plus the energy liberated by the carbonation reaction, as well as the energy liberated by the mixing system, are sufficient to maintain the desired reaction temperature without any external heating or cooling.

Concentration of Active Agent in the Carbonation Step

To simplify the calculations of how much active agent is needed in the process and how much of it may be included in the product of the present invention, we prefer to use the weights of the respective acids, since the carboxylate moieties differ from their respective acids by less than 1%. Therefore, in cases that suitable ketenes, esters, carboxylate salts, acid anhydrides and/or acyl halides are being used, the equivalent weight of the respective acid should be calculated, unless otherwise indicated. Moreover, as we are presently not aware of differences among the activities of the acids of the general formula $CH_3(CH_2)_nCOOH$, wherein n=7, 8, and 9, including mixtures thereof, their individual contribution to the total weight of the active agent should be calculated arithmetically, namely by adding the weight of each individual acid as if these are of the same chemical entity. This concept is important for understanding this invention and particularly the claims, unambiguously. The difference between the molecular weights of the respective acids (~±10%) is not a great problem, because a person skilled in the art will in any event operate the process in a manner which is not sensitive to even larger variations of the concentrations of the active agent, namely, of >±10 wt. %, based on $CaCO_3$. Moreover, when using decanoic acid as the presently preferred active agent, the present invention will not even be subject to the above-mentioned inaccuracy.

To determine the concentration range of the active agent in the present invention, it is important to be aware of the various functions of this agent in the production process and the effects that it produces in the final product.

The prior art describes many additives that assist in producing particulate precipitated aragonite, but none of these additives is comparable to the present active agent for the following two major reasons:

1. The active agent leads to a dramatic reduction of the specific gravity of the particulate product and allows use of the flotation method to separate the "light" particulate precipitated aragonite, from the "heavy" contaminants (containing aluminosilicates and heavy metal salts, carbonates and oxides). These "heavy" particles sink down to the bottom of the carbonator/flotation cell and are discharged from the production unit without reaching the downstream filter, and 2. The optical properties of the particulate precipitated aragonite product are altered and its effective refractive index is increased dramatically.

Thus, the pure product of the present invention, on the flotation embodiment, is being carried to the top of the reactor/carbonator/flotation cell, by the small bubbles that adhere to the tiny precipitated aragonite particles, and this relatively pure product is discharged from the top of the carbonator/flotation cell prior to any downstream operation. Thus, in this embodiment, the present process entails an intrinsic, built-in, extra purification operation, prior to the downstream dewatering operation, which is not so common in the prior art.

This unique property of the active agent to cause the flotation of the "light" particulate precipitated aragonite, is also a reason why this embodiment of the present invention is superior over any of the prior art production technologies in exploiting highly contaminated sources of $CaCO_3/CaO$, which have hitherto been unsuitable as raw materials for production of a particulate precipitated aragonite, of filler, extender and pigment quality grades. Such sources can now be utilized successfully, using this novel technology of the present invention.

Since the aqueous calcium hydroxide slurry is usually quite contaminated and the impurities are liable to affect performance of the active agent, the threshold (minimum) concentration of the active agent will vary, but is within the competence of a skilled person to determine, under any particular set of circumstances. In any case, it is desirable to avoid this threshold concentration at the carbonation stage, as this is a point of instability and would involve unnecessary risk to the desired objective. When considering use of a new feedstock of $CaCO_3/CaO$, laboratory experiments will reveal the minimum concentration of the active agent, which is necessary to start the production of particulate precipitated aragonite, without any faults (vis-a-vis the pertinent $CaCO_3/CaO$ feedstock). This value is expected to be in most cases above 0.2 wt. %, preferably within the range 0.4% to 3 wt. %, based on the calcium carbonate.

It is very important to note that this threshold concentration, discussed above, for catalyzing the production of particulate precipitated aragonite of the present invention (~0.2% wt. %, based on $CaCO_3$) is substantially above the threshold concentration that is required to cause the flotation of this product in aqueous solutions (~0.02% wt. %, based on $CaCO_3$) and that by operating in the concentration range merely for a "proper" flotation process, nothing that is disclosed in the present invention really happens. Actually, the optimal physical and chemical properties of the particulate precipitated aragonite calcium carbonate of the present invention are attained at above 100 fold of this concentration (~2–3 wt. %, based on $CaCO_3$).

Other factors may indicate use of even higher concentrations of the active agent in the production process of the present invention. For instance, coating the surface of the particulate precipitated aragonite, with a predetermined rather thick layer of the active agent, in situ, in a carbonator/flotation cell, may require quite high concentrations of this material, which may exceed 5%, 10% and even 15 wt. %, based on $CaCO_3$, in order to produce good surface coated hydrophobic and acid resistant particulate precipitated aragonite (e.g. for master batches). Naturally, at such high active agent concentrations, the cost component of the coating should then be compared to the alternative possibilities of downstream coating, which are also available in the prior art, as well as in the present invention (c.f. FIGS. 1 and 2, respectively). Another serious reason to avoid operating the process at too low concentrations, is the fact that the chemical and physical properties of the product, and especially its optical properties and specific gravity (which may well be interdependent), are dramatically affected by the concentration of the active agent.

In between the upper limit and the threshold limit of the concentration of the active agent in the process of the present invention, the optimum concentration should also be determined by one skilled in this art, either vis-a-vis the quality of the $CaCO_3/CaO$, or whenever the properties of the product are to be changed. The active agent is not an expensive material, but still it may throw an economical burden on the total cost of the final product due to the fact that particulate precipitated aragonite is a relatively inexpensive material.

Intuitively, the concentration of 10 wt. %, based on the calcium carbonate, seems to be an economical upper limit of the active agent, while 0.2 wt. %, wt; based on the $CaCO_3$, seems to be its threshold (minimum) concentration.

Carbon Dioxide in the Carbonation Step

Use of carbon dioxide gas or a carbon dioxide containing gas is well known in the prior art methods for producing precipitated calcium carbonate particles. The process of the present invention is similar in this respect to the prior art processes that operate with substantially pure carbon dioxide gas as well as with mixtures of carbon dioxide with up to about 90 wt. % inert gases (e.g. air). At lower concentrations of the carbon dioxide in the gas (<10 wt. %), however, the efficiency of the process may be too low.

Additives in the Process

The process of the present invention is quite self-sufficient and requires only the active agent in suitable quantities, as discussed above. The active agent can be introduced preferably already premixed with the aqueous calcium hydroxide slurry, or alternatively (or additionally) it can be introduced directly into the carbonator. The active agent can also be used downstream the carbonation stage, but that, naturally, has no effect on the production of particulate precipitated aragonite in the carbonator.

It appears that the active agent has a surprising affinity to the aragonite which is unlikely to be adversely affected by the presence of other additives. Consequently, additives like phosphoric acids and water soluble salts thereof, can be used in the present invention to modify the product properties by increasing the aspect ratio of the thus formed acicular crystals; polyacrylates and some short-chain carboxylic acids can be used to modify the rheology of the product mixtures and allow operation at higher calcium hydroxide concentrations and, consequently, at higher throughputs; and chelating agents can be used to convert heavy metals into water-soluble species and once again lead to super-pure particulate precipitated aragonite.

It is nevertheless prudent to check carefully the effect that well known additives of the prior art may have on the action of the active agent, but in most cases the active agent will be the dominant catalyst for the purpose of the present invention and, therefore, such additives can usually be introduced at various stages of the process, as is customary in the prior art (c.f. FIGS. 2 and 3).

The Mixing System

The need for high shear mixing in this process is well known in the relevant art. The mixers may be a rotor/stator type or a rotor only type. Usually, the latter one is used to produce relatively larger product particles, while the rotor/stator type leads to much higher attrition of the acicular crystals. On the other hand, the rotor/stator type may allow a more efficient dispersion of the gas bubbles, thereby improving the quality of the product. The skilled operator will utilize the preferred mixing system for working or enhancing the present process. The type of mixers and the rotor speed should be optimized according to the desired carbonation performance and the desired product characteristics.

The lower limit of the rotor speed (hereinafter—"Tip Speed" or "Peripheral Speed") is known in the prior art. A requirement of a minimum tip speed of about 5 m/sec., to effect the formation of desired product is not unusual in this art.

The upper limit of the rotor speed is determined by mixer technology, cost of the specific mixer, the nature of the desired product and the energy that is to be used. For instance, the higher the rotor speed, the lower may be the reaction time (in a continuous process, the reaction time is termed HUT (Hold Up Time) and it is calculated as follows: HUT=V (the carbonator volume)/F (the discharge rate of the product mixture out of the carbonator)). This in turn may lead to small particles. A skilled person in this art will know how to optimize the kind of mixers and rotor speeds above the minimal peripheral speed, which is preferably 5 m/sec

The Reaction Duration in the Reactor/Carbonator/Flotation Cell

As already mentioned above, the carbonation step is preferably conducted in a continuous mode of operation. In such a case, "reaction duration" is hardly relevant, but we can calculate the HUT (Hold Up Time), which lies essentially within the range between 5 minutes and 180 minutes. At below the lower limit of the HUT the yields may be too low and the PSD (Particle Size Distribution) of the product may be too small, while at the upper limit of the HUT the yields may be excellent, but the PSD may also be too small, because of excessive attrition of the product in the flotation cell. Once again, the skilled person will be able to determine by experiment, suitable working parameters vis-a-vis the desired product properties and to optimize its quality and cost.

The present invention will now be described in more detail by way of Examples, which are presented for illustration purposes only and are not be construed restrictively.

Experimental

Raw Materials:
A. All raw materials were purchased from Aldrich, unless otherwise specified.
B. Ethyl decancate was prepared by reacting decanoyl chloride with ethanol in the presence of triethylamine at about 50° C. After about 3 hours the product was washed with water to remove water-soluble residues and it was then dried at about 50° C. under a vacuum of about 30 mm/Hg.
C. Sodium decanoate was prepared by thoroughly mixing decanoic acid with 2% aqueous NaOH at about 70° C. until the pH passed 10.
D. Potassium decanoate was prepared by thoroughly mixing decanoic acid with 2% aqueous KOH at about 70° C. until the pH passed 10.
E. CaO(1)—of Arad, Israel. F. CaO(2)—of Shfeya, Israel.
G. Commercial PCC—Aragonite; of Specialty Minerals Inc. (SMI); Opacarb® A40.
H. $CO_2$—Cylinders of 100% pure compressed gas of Mifalay Hamzan Ltd., Haifa.
I. The Paint Constituents:
  Nopco NDW of Henkel
  Cellosize QP 15000 (hydroxy ethyl cellulose) of Union Carbide
  Disperse One (45%. N.V.) of Tambur, Israel
  Synperonic NP10 of ICI
  $TiO_2$ (Kronos 2160) of Kronos (However, similar $TiO_2$ pigments, like Tioxide R-TC90
  and Tioxide TR92, of which their $D_{50}$=220 nm±20 nm may serve equally well)
  Synthetic sodium aluminum silicate (p820) of Degussa
  Kaolin clay ($D_{50}$=3.1 micron) of Engelhard
  $CaCO_3$ powder ($d_{50}$=3.5 microns) of Polychrom, Israel—"Girulite-8"
  Talc ($D_{50}$=12.3 micron) of Lusenac Val Chisone
  Copolymer vinyl acetate acrylate emulsion (55% N.V.) of Cerafon, Israel
  Butyl diglycol acetate of Union Carbide
  Kathon LXE of Rohm & Haas
  Ammonia (25%) of Frutarom, Israel
Instruments and Accessories:
1. pH meter/controller; Jenco; Model 3671; Made in China.
2. pH electrode; Hanna Industries; type HI 1131B (Glass Probe).
3. Thermometer; Jenco Model 3671; Made in China.
4. Peristaltic pump; Watson-Marlow; Model 505u (variable speed).
5. Agitator; Ika; Model RW-20 (variable speed).
6. Dissolver; Hsiangtal; Model HD-550; Made in Taiwan
7. Ultra-turrax® T50; Ika; rotor d=3.8 cm; stator d=4 cm.
8. Disk type rotor of d=12 cm.
9. Disk type rotor of d=8 cm.
10. Saw-blade type rotor of d=9 cm.
11. Saw-blade type rotor of d=4.8 cm.
12. Hydrocyclone 2"; Mozely; P=50 psi; vortex finder=11 mm; spigot=6.4 mm.
13. Vacuum pump; Vacuumbrand GmbH; Model MD 4C.
14. Buchner+filter cloth with 8–10 μm pores.
15. XRD (X-Rays Diffractometer); Siemens D-500 for the crystallographic phases.
16. SEM (Scanning Electron Microscope); Jeol 5400 for the shapes of the particles.
17. Colorimeter; Hunterlab D25-PC2 for whiteness measurements.
18. Colorimeter; ACS instrument (Applied Color Systems).
19. Ultrasonic bath (10 l); Selecta, Spain—"ULTRASONS".
20. Analytical Balance; Shekel Ltd., Israel.
21. HPLC Analyzer; Waters HPLC Analyzer (Detector 486+Autosampler 717+Pump 510+millenium Software).
22. HPLC Column; Phenomenex C18(250 mm×4.3 mm; 5 μm Particle size).

PREPARATION I

Preparation of Aqueous Calcium Hydroxide Slurries

The aqueous calcium hydroxide slurry was prepared in the laboratory in a batch mode of operation as follows: 40 kg of tap water were introduced into a 50 l stainless steel 316 reactor that was equipped with a steam heated jacket, a thermometer and with the Hsiangtal Dissolver with a rotor of d=12 cm. The Dissolver was operated at 200 rpm, 4 kg of CaO (Shfeya) were added to the reactor during less than 10 minutes and the slurry was allowed to stir for 10–80 minutes. At that time the temperature rose to above 60° C. and when it reached its maximal temperature at 80–90° C., the mixture was ready for its purification prior to the carbonation stage, as follows:

a. The slurry passed a stainless steel 316 screen to remove particles of d>2 mm, and
b. The filtered slurry passed a hydrocyclone to remove particles of d>50 μm.

Notes:

At this point the warm aqueous calcium hydroxide slurry was ready for its use in the carbonation stage and its temperature was maintained at a preset value by heating the slurry in the above reactor in order to control the temperature in the carbonator.

The potential active agent(s) and any optional additives could be blended into the warm slurry at a preset concentration before the purification steps a. and b. or thereafter.

This batch mode of operation is used only in the laboratory tests. The production plant is intended to be operated under a continuous mode of operation, as is discussed herein.

PREPARATION II

Preparation of Aqueous Calcium Hydroxide Slurries

PREPARATION I was repeated using CaO of Arad, a substantially purer raw material than that of Shfeya (the respective whitenesses are >95% and ~88%).

EXAMPLE 1

Screening Test for the Potential Active Agents

Possible active agents were investigated by producing particulate precipitated calcium carbonate according to the following procedure:

2 kg tap water were added to a 3.2 l stainless steel 316 reactor (of inner diameter d=15 cm and length ~18 cm), equipped with a steam heated jacket, a pH electrode, a thermometer and the Hsiangtal Dissolver with a saw-blade rotor of d=4.8 cm (c.f. FIG. 3). The Dissolver was operated at a preset speed and carbon dioxide gas or a carbon dioxide containing gas and the aqueous calcium hydroxide slurry of PREPARATION I, containing already the active agent, were fed simultaneously into the reactor, while maintaining the pH, the temperature and the production rate at preset values. The product was collected at the top of the reactor, and the impurities were discharged from the bottom of the reactor (naturally, the product exited from the bottom of the reactor when the experimental active agent did not lead to a particulate precipitated aragonite and to its flotation).

The first 10 l of resulting slurry were discarded. The residual slurry was collected and it was filtered through a filter-cloth on the Buchner using a vacuum pump to dewater the product. The filter cake was dried for 12 hours at 120° C. and the crystallographic morphologies and the shapes of the crystals of the precipitated calcite and/or aragonite calcium carbonate particles were determined using XRD and SEM analyses, respectively. The results are shown in the Table 1, below.

The Process Set Points—Continuous Mode of Operation:
1. Rotor Speed=4000 rpm (Tip Speed ~10 m/sec.).
2. pH=9.5.
3. Temperature=85° C.
4. Carbon dioxide flow rate=180 L.P.H. (liters/hour).
5. Aqueous calcium hydroxide slurry (of Shfeya) –10% (wt)=-~6 L.P.H. (to maintain the preset pH value).
6. Potential active agent concentration 1 wt. %, based on $CaCO_3$.

TABLE 1 the results of EXAMPLE 1

| Test # | Active Agent | Number of Carbons | Product (Isomorph) |
|---|---|---|---|
| 1 | Propionic acid | 3 | Calcite |
| 2 | Lactic acid | 3 | Calcite |
| 3 | Pyruvic acid | 3 | Calcite |
| 4 | Acrylic acid | 3 | Calcite |
| 5 | Methoxyacetic acid | 3 | Calcite |
| 6 | Methacrylic acid | 4 | Calcite |
| 7 | Butanoic acid | 4 | Calcite |
| 8 | Pentanoic acid | 5 | Calcite |
| 9 | Hexanoic acid | 6 | Calcite |
| 10 | Heptanoic acid | 7 | Calcite |
| 11 | Octanoic acid | 8 | Calcite |
| 12 | Phthalic acid | 8 | Calcite |
| 13 | Terephthalic acid | 8 | Calcite |
| 14 | 2-Ethylhexanoic acid | 8 | Calcite |
| 15 | Nonanoic acid | 9 | Aragonite |
| 16 | Nonanoic acid* | 9 | Aragonite |
| 17 | Azelaic acid | 9 | Calcite |
| 18 | Trimelitic acid | 9 | Calcite |
| 19 | Decanoic acid | 10 | Aragonite |
| 20 | Decanoic acid* | 10 | Aragonite |
| 21 | Sodium decanoate | 10 | Aragonite |
| 22 | Potassium decanoate | 10 | Aragonite |
| 23 | Ethyl decanoate | 12 | Aragonite |
| 24 | Decanoyl chloride | 10 | Aragonite |
| 25 | Decanoic acid anhydride | 20 | Aragonite |
| 26 | Undecanoic acid | 11 | Aragonite |
| 27 | Undecanoic acid* | 11 | Aragonite |
| 28 | 4-Butylbenzoic acid | 11 | Calcite |
| 29 | Dodecanoic acid | 12 | Calcite |
| 30 | Palmitic acid | 16 | Calcite |
| 31 | Stearic acid | 18 | Calcite |
| 32 | Oleic acid | 18 | Calcite |
| 33 | $MgCl_2$ | — | Calcite |
| 34 | $AlCl_3$ | — | Calcite |
| 35 | $C_{12}H_{25}C_6H_4SO_3H$ (LABSA) | 18 | Calcite |

*Was pumped continuously and directly into the carbonator.

EXAMPLE 2

A Screening Test for Interfering Compounds

EXAMPLE 1 was repeated, except that in all the experiments 1% (wt; based on the calcium carbonate) decanoic acid was premixed in the aqueous calcium hydroxy slurry feed and in each experiment an additional experimental active agent was added to study its effect on the activity of the decanoic acid. The results are shown Table 2, below.

The Process Set Points—Continuous Mode of Operation:

1. Rotor Speed=4000 rpm (Tip Speed ~10 m/sec.)
2. pH=9.5. 3. Temperature=85° C.
4. Carbon dioxide flow rate 180 L.P.H. (liters/hour).
5. Aqueous calcium hydroxide slurry (of Shfeya) –10% (wt)=-~6 L.P.H. (to maintain the preset pH value).
6. Active agents concentrations=1 wt. % decanoic acid+1 wt. % potential active agent based on $CaCO_3$.

TABLE 2 the results of EXAMPLE 2

| Test # | Active Agent | Number of Carbons | Product (Isomorph) |
|---|---|---|---|
| 1 | Propionic acid | 3 | Aragonite |
| 2 | Lactic acid | 3 | Aragonite |
| 3 | Pyruvic acid | 3 | Aragonite |
| 4 | Acrylic acid | 3 | Aragonite |
| 5 | Methoxyacetic acid | 3 | Aragonite |
| 6 | Methacrylic acid | 4 | Aragonite |
| 7 | Butanoic acid | 4 | Aragonite |
| 8 | Pentanoic acid | 5 | Aragonite |
| 9 | Hexanoic acid | 6 | Aragonite |
| 10 | Heptanoic acid | 7 | Aragonite |
| 11 | Octanoic acid | 8 | Aragonite |
| 12 | Phthalic acid | 8 | Calcite |
| 13 | 2-Ethylhexanoic acid | 8 | Aragonite |
| 14 | Nonanoic acid | 9 | Aragonite |
| 15 | Azelaic acid | 9 | Aragonite |
| 16 | Trimelitic acid | 9 | Calcite |
| 17 | Decanoic acid | 10 | Aragonite |
| 18 | Undecanoic acid | 11 | Aragonite |
| 19 | 4-ButylBenzoic acid | 11 | Aragonite |
| 20 | Dodecanoic acid | 12 | Aragonite |
| 21 | Palmitic acid | 16 | Aragonite |
| 22 | Stearic acid | 18 | Aragonite |
| 23 | Oleic acid | 18 | Aragonite |
| 24 | $MgCl_2$ | — | Aragonite |
| 25 | $AlCl_3$ | — | Aragonite |
| 26 | $C_{12}H_{25}C_6H_4SO_3H$ (LABSA) | 18 | Aragonite |

EXAMPLE 3

A Batch Mode of Operation

A batch mode of operation, of which parameters were as close as possible to those of EXAMPLE 1, was attempted. Only particulate precipitated calcite of rhombohedral shape was obtained. No particulate precipitated aragonite could be obtained when using decanoic acid or any other active agent that was mentioned as being effective in EXAMPLE 1. The experiment was conducted as follows:

The active agents were investigated by producing precipitated calcium carbonate particles according to the following procedure:

2 kg aqueous calcium hydroxide slurry, containing already the respective active agent (c.f. EXAMPLE I) were added to the 3.2 l stainless steel 316 reactor of EXAMPLE 1. The Dissolver was operated at 4000 rpm, the temperature was maintained at 85° C. and the production rate was determined by controlling the feed rate of the carbon dioxide gas. The carbonation was stopped after about 20–30 minutes, when the pH reached 7. The product mixture was then removed from the reactor through its bottom outlet.

The resulting slurry was filtered through a filter cloth on the Buchner using a vacuum pump to dewater the product. The filter cake was dried for 12 hours at 120° C. and the crystallographic morphologies and the shapes of the crystals of the precipitated calcite particles were determined using XRD and SEM analyses, respectively. As mentioned above, no precipitated aragonite particles were obtained.

The Process Set Points—Batch Mode of Operation:
1. Rotor Speed=4000 rpm (Tip Speed ~10 m/sec.).
2. pH=~14 7.
3. Temperature=85° C.
4. Carbon dioxide flow rate=180 L.P.H. (liters/hour).
5. Aqueous calcium hydroxide slurry (of Shfeya) –10% (wt)=2 kg.
6. Potential active agent concentration=1 wt. %, based on $CaCO_3$.

EXAMPLE 4

Parametric Studies—the Effect of the Temperature

Similar experiments to EXAMPLE 1 were conducted using decanoic acid only. The results are as follows:
The Process Set Points—Continuous Mode of Operation:
1. Rotor Speed=4800 rpm (Tip Speed ~12 m/sec.).
2. pH=9.5.
3. Temperature=variable.
4. Carbon dioxide flow rate=180 L.P.H. (liters/hour).
5. Aqueous calcium hydroxide slurry (of Shfeya) –10 wt. %=~6 L.P.H. (to maintain the preset pH value).
6. Active agent concentration=decanoic acid; 0.5 wt. %, based on $CaCO_3$.

TABLE 3 the results of EXAMPLE 4

| Test # | Temperature ° C. | Mineralogical Phase XRD |
|---|---|---|
| 1 | 87 | Aragonite |
| 2 | 80 | Aragonite |
| 3 | 70 | Aragonite |
| 4 | 60 | Aragonite |
| 5 | 50 | Calcite |

EXAMPLE 5

Parametric Studies—Effect of the pH

Similar experiments to EXAMPLE 1 were conducted using decanoic acid only. The results are as follows:
The Process Set Points—Continuous Mode of Operation:
1. Rotor Speed=4800 rpm (Tip Speed ~12 m/sec.).
2. pH=variable.
3. Temperature=87° C.
4. Carbon dioxide flow rate=180 L.P.H (liters/hour)
5. Aqueous calcium hydroxide slurry (of Shfeya) –10 wt %=~6 L.P.H. (to maintain the preset pH value).
5. Active agent concentration=decanoic acid; 0.5 wt. % based on $CaCO_3$.

TABLE 4 the results of EXAMPLE 5

| Test # | pH | Mineralogical Phase XRD |
|---|---|---|
| 1 | 10 | Aragonite |
| 2 | 9.5 | Aragonite |
| 3 | 9 | Aragonite |
| 4 | 8.5 | Aragonite |
| 5 | 8.0 | Calcite |
| 6 | 7.0 | Calcite |

EXAMPLE 6

Parametric Studies—Concentration Effect of the Active Agent

Similar experiments to EXAMPLE 1 were conducted using decanoic acid only. The results are as follows:
The Process Set Points—Continuous Mode of Operation:
1. Rotor Speed=4800 rpm (Tip Speed ~12 m/sec.).
2. pH=9.5. 3. Temperature=87° C.
4. Carbon dioxide flow rate=180 L.P.H. (liters/hour).

5. Aqueous calcium hydroxide slurry (of Shfeya) ~10% (wt)=~6 L.P.H. (to maintain the preset pH value).
6. Active agent concentration=decanoic acid; variable wt. %; based on $CaCO_3$.

TABLE 5 the results of EXAMPLE 6

| Test # | Decanoic acid % (wt) | Mineralogical Phase XRD |
|---|---|---|
| 1 | 1.0 | Aragonite |
| 2 | 0.5 | Aragonite |
| 3 | 0.3 | Aragonite + Calcite* |
| 4 | 0.2 | Aragonite + Calcite* |
| 5 | 0.1 | Calcite |

*A crystallographic purity (aragonite/(aragonite + calcite)) < 90%.
Note: Though the present invention is especially aimed at obtaining substantially pure particulate precipitated aragonite calcium carbonate of crystallographic purity (aragonite phase/(aragonite phase + calcite phase)) ≧90% and even > 95%, there are still applications that can utilize mixtures of these isomorphs where such crystallographic purity is < 90%, and such mixtures are within the scope of the present invention. In such cases the boundary conditions of the present invention (c.f. Tests #3 and #4, above) may still be used.

EXAMPLE 7

Parametric Studies—Concentration Effect of the Ca(OH)$_2$

Similar experiments to EXAMPLE 1 were conducted using decanoic acid only. The results are as follows:
The Process Set Points—Continuous Mode of Operation:
1. Rotor Speed=4800 rpm (Tip Speed ~12 m/sec.).
2. pH=9.5.
3. Temperature=87° C.
4. Carbon dioxide flow r=180 L.P.H. (liters/hour)
5. Aqueous calcium hydroxide slurry (of Shfeya) –variable wt. %=~variable L.P.H. (to maintain the preset pH value).
6. Active agent concentration=decanoic acid; 0.5 wt. % based on $CaCO_3$.

TABLE 6 the results of EXAMPLE 7

| Test # | Solids in Slaked Lime % (wt) | Mineralogical Phase XRD |
|---|---|---|
| 1 | 8 | Aragonite |
| 2 | 4 | Aragonite |
| 3 | 3 | Aragonite + Calcite* |
| 4 | 2 | Aragonite + Calcite* |
| 5 | 1 | Calcite |

*A crystallographic purity (aragonite : (aragonite + calcite)) < 90% and c.f. the above note at the end of Example 6.

EXAMPLE 8

Parametric Studies—Rotor Speed Effect

Similar experiments to EXAMPLE 1 were conducted using decanoic acid only. The results are as follows:
The Process Set Points—Continuous Mode of Operation:
1. Rotor Speed=variable rpm (Tip Speed ~variable).
2. pH=9.5.
3. Temperature=87° C.
4. Carbon dioxide flow rate=180 L.P.H (liters/hour).
5. Aqueous calcium hydroxide slurry (of Shfeya) –10 wt. %=~6 L.P.H. (to maintain the preset pH value).
6. Active agent concentration=decanoic acid; 0.5 wt. % based on $CaCO_3$.

TABLE 7 the results of EXAMPLE 8

| Test # | Rotor Speed rpm | Tip Speed m/sec. | Mineralogical Phase XRD |
|---|---|---|---|
| 1 | 10000 | 25 | Aragonite |
| 2 | 4800 | 12 | Aragonite |
| 3 | 2000 | 5 | Aragonite + Calcite* |
| 4 | 1000 | 2.5 | Calcite |

*A crystallographic purity (aragonite : (aragonite + calcite)) < 90% and c.f. the above note at the end of Example 6.

EXAMPLE 9

Parametric Studies—Effect of the $CO_2$ Flow Rate (F.R.)

Similar experiments to EXAMPLE 1 were conducted using decanoic acid only. The results are as follows:
The Process Set Points—Continuous Mode of Operation:
1. Rotor Speed=4800 rpm (Tip Speed ~12 m/sec.).
2. pH=9.5.
3. Temperature=87° C.
4. Carbon dioxide flow rate=variable L.P.H. (liters/hour)
5. Aqueous calcium hydroxide slurry (of Shfeya) –variable wt. %=~variable L.P.H. (to maintain the preset pH value).
6. Active agent concentration decanoic acid; 0.5 wt. % based on $CaCO_3$.

TABLE 8 the results of EXAMPLE 9

| Test # | $CO_2$ Flow Rate L.P.H. | Mineralogical Phase XRD |
|---|---|---|
| 1 | 240 | Aragonite |
| 2 | 180 | Aragonite |
| 3 | 120 | Aragonite |

EXAMPLE 10

Parametric Studies—Effect of the $CO_2$/Air Ratio

Similar experiments to EXAMPLE 1 were conducted using decanoic acid only. The results are as follows:
The Process Set Points—Continuous Mode of Operation:
1. Rotor Speed=4800 rpm (Tip Speed ~12 m/sec.).
2. pH=9.5.
3. Temperature=87° C.
4. Carbon dioxide flow rate=180 L.P.H. (liters/hour).
5. Aqueous calcium hydroxide slurry (of Shfeya) ~10% (wt)=~6 L.P.H. (to maintain the preset pH value.
6. Active agent concentration=decanoic acid; 0.5 wt. %; based on $CaCO_3$.
7. Air=variable

TABLE 9 the results of EXAMPLE 10

| Test # | Air/$CO_2$ | Mineralogical Phase XRD |
|---|---|---|
| 1 | 0 | Aragonite |
| 2 | 0.33 | Aragonite |
| 3 | 0.66 | Aragonite |

EXAMPLE 11

The Effect of Active Agent on Content of the Wet Filter Cake

Similar experiments to EXAMPLE 1 were conducted using decanoic acid only. The content of $CaCO_3$ in the wet filter cake was determined after drying 12 hours at 120° C. Relatively pure (aragonite phase/(aragonite phase+calcite phase))>95% and dry precipitated acicular aragonite calcium carbonate particles were obtained. The results are as follows:

The Process Set Points—Continuous Mode of Operation:
1. Rotor Speed=4800 rpm (Tip Speed ~12 m/sec.).
2. pH=9.5.
3. Temperature=90° C.
4. Carbon dioxide flow rate=180 L.P.H. (liters/hour).
5. Aqueous calcium hydroxide slurry (of Shfeya) ~10 wt. %=~6 L.P.H. (to maintain the preset pH value).
6. Active agent concentration=decanoic acid; 0.7; 1.0; 2.0 wt. %; based on $CaCO_3$.

TABLE 10 the results of EXAMPLE 11

| Test # | Dosage % (wt) | Product (Isomorph) | $CaCO_3$ % (wt)* | Crystallographic Purity** |
|---|---|---|---|---|
| 1 | 0.7 | Aragonite | >80 | ≧95% |
| 2 | 1.0 | Aragonite | >80 | ≧95% |
| 3 | 2.0 | Aragonite | >80 | ≧95% |

Figure 4:
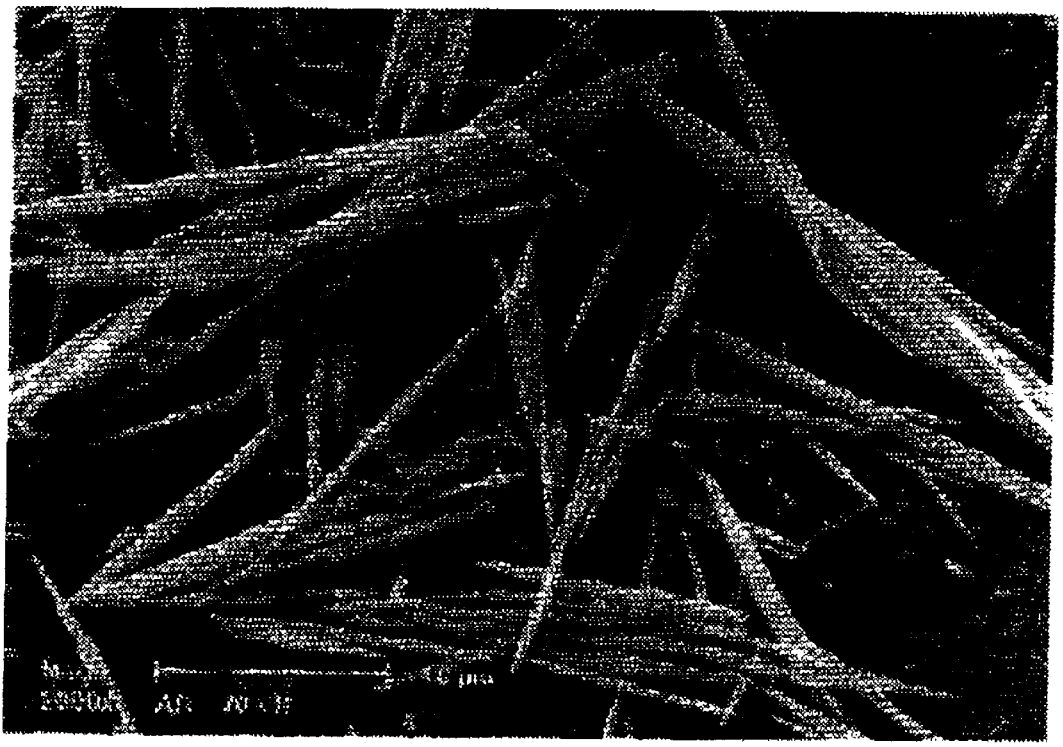
FIG. 4 shows a SEM picture of a particulate precipitated aragonite, in accordance with an embodiment of the present invention.
Figure 5:
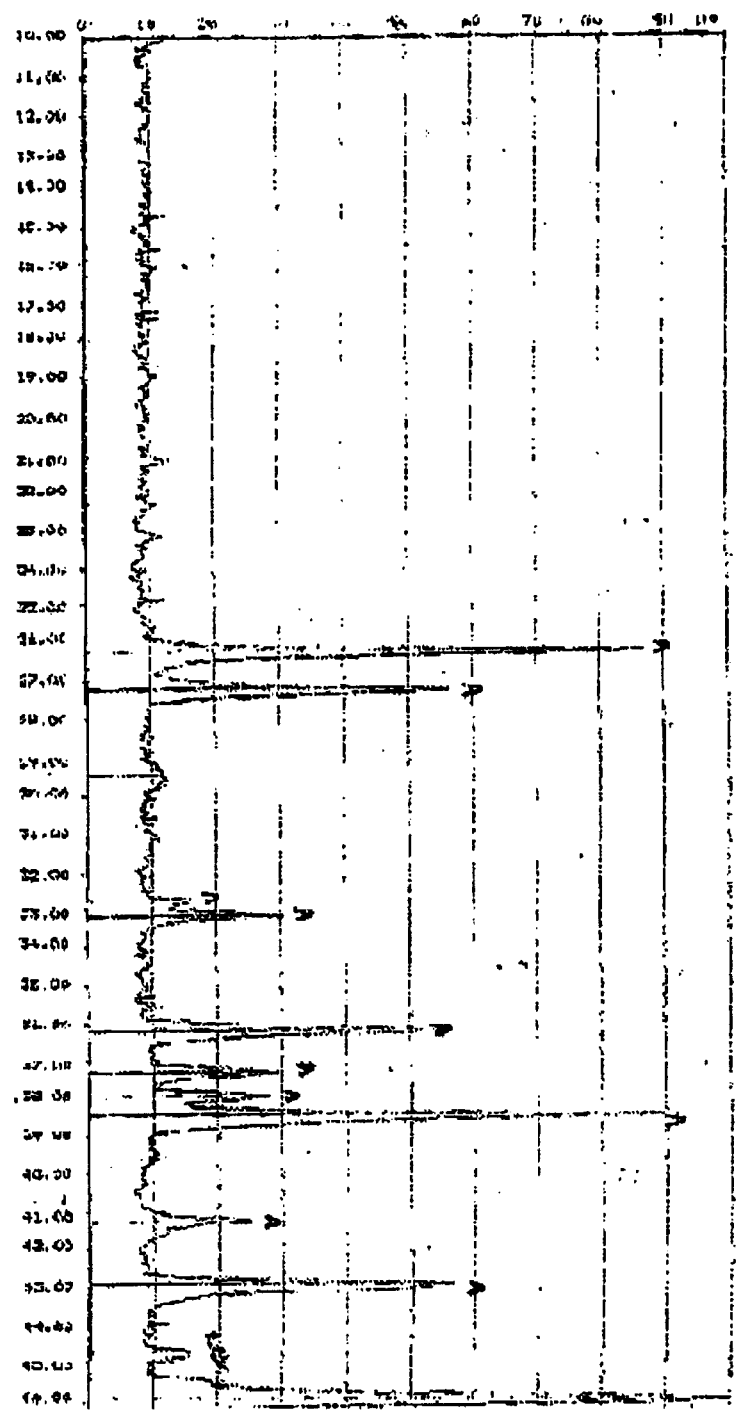
FIG. 5 shows an XRD spectrum of a particulate precipitated aragonite, in accordance with an embodiment of the present invention.

*% (wt) $CaCO_3$ = 100 × wt. of dry filter cake / wt. of wet filter cake
**As determined by the XRD analyses (for Test #2 - c.f. FIGS. 4 and 5)
Note:
By choosing relatively standard conditions for the present process, it is possible to reduce the water content in the wet filter cake below 20 wt. %.

EXAMPLE 12

The Effect of the Active Agent on the Resistivity to Acids

Similar experiments to EXAMPLE 1 were conducted using decanoic acid only, the resistivity of the dry samples to acidic aqueous solutions being determined as follows. A 5 l solution of HCl in water at pH=3.5 was prepared for all the following experiments, so as to assure equal starting experimental conditions. 100 ml of this HCl solution were poured into a 100 ml graduated cylinder, 5 g of precipitated $CaCO_3$ particles were added and the pH was measured after 20 minutes. Evolution of $CO_2$ was observed visually, as was the behavior of the commercial sample #C, the calcite #BM-37, and it was found that the aragonite samples of the present invention (#12-3, #12-4, #12-5) were markedly different. It is worthwhile to note that sample #12-5 produced few bubbles that did not detach from the surface of the precipitated aragonite particles. The results are as follows:

The Process Set Points—Continuous Mode of Operation:
1. Rotor Speed=5200 rpm (Tip Speed ~13 m/sec.).
2. pH=9.5. 3. Temperature=90° C.
3. Carbon dioxide flow rate=180 L.P.H. (liters/hour).
4. Aqueous calcium hydroxide slurry (of Shfeya) ~10 wt. %=~6 L.P.H. (to maintain the preset pH value).
5. Active agent concentration decanoic acid; 0.7%; 1.0%; 2% wt. % based on $CaCO_3$.

TABLE 11 the results of EXAMPLE 12

| Test # | Sample # | Active agent (wt. %) | Product (Isomorph) | pH after 20 mins. | Note |
|---|---|---|---|---|---|
| 1 | C* | Unknown | Aragonite | >6 | Violent Evolution of $CO_2$ |

TABLE 11-continued the results of EXAMPLE 12

| Test # | Sample # | Active agent (wt. %) | Product (Isomorph) | pH after 20 mins. | Note |
|---|---|---|---|---|---|
| 2 | BM-37** | 1.0 | Calcite | >5 | Evolution of $CO_2$ |
| 3 | 12-3 | 0.7 | Aragonite | <4 | Slight Evolution of $CO_2$ |
| 4 | 12-4 | 1.0 | Aragonite | <4 | Slight Evolution of $CO_2$ |
| 5 | 12-5 | 2.0 | Aragonite | <4 | No Evolution of $CO_2$ |

*Commercial PCC - Aragonite; of Specialty Minerals Inc. (SMI); OpacarbPLUS CODE 121 IS NOT DEFINED® A40
**This sample was taken from the batch mode of operation in EXAMPLE 3
Note:
By choosing relatively standard conditions for the present process, it is possible to increase the resistance of the product towards acids by using quite low concentrations of the active agent and obtain excellent product for the paper industry of which processes are acidic and for the coating industry for durable paints for acidic environments.

EXAMPLE 13

Effect of Raw Material/Process on Whiteness of the Product

EXAMPLE 1 and EXAMPLE 3 were conducted using the aqueous calcium hydroxide slurries of PREPARATION I and of PREPARATION II for comparison. The whitenesses of the products are compared.

The results are as follows:

The Process Set Points—Continuous Mode of Operation:
1. Rotor Speed=4000 rpm (Tip Speed ~10 m/sec.).
2. pH=9.5.
3. Temperature=85° C.
4. Carbon dioxide flow rate=180 L.P.H. (liters/hour)
5. Aqueous calcium hydroxide slurry (of Arad/Shfeya) ~10 wt. %=~6 L.P.H. (to maintain the preset pH value).
6. Active agent concentration=decanoic acid; 1 wt. % based on $CaCO_3$.

The Process Set Points—Batch Mode of Operation:
1. Rotor Speed=4000 rpm (Tip Speed ~10 m/sec.).
2. pH=~14→7. 3. Temperature=85° C.
3. Carbon dioxide flow rate=180 L.P.H. (liters/hour).
4. Aqueous calcium hydroxide slurry (of Arad/Shfeya) ~10 wt. %=2 kg.
5. Active agent concentration decanoic acid 1 wt. % based on $CaCO_3$.

TABLE 12 the results of EXAMPLE 13

| CaO of Arad (whiteness = >95%) | | CaO of Shfeya (whiteness = ~88%) | |
|---|---|---|---|
| Continuous | Batch | Continuous | Batch |
| AR-83A Aragonite $CaCO_3$ | BM37A Calcite $CaCO_3$ | AR-83 Aragonite $CaCO_3$ | BM37 Calcite $CaCO_3$ |

TABLE 12-continued the results of EXAMPLE 13

| CaO of Arad (whiteness = >95%) | | CaO of Shfeya (whiteness = ~88%) | |
|---|---|---|---|
| Continuous | Batch | Continuous | Batch |
| Whiteness = 98–9% | Whiteness = 97–8% | Whiteness = 97–9% | Whiteness = 92–5% |

Notes:
1. When the raw material (CaO) is relatively pure, the whiteness of the products (AR-83A and BM37A) is not (and should not be) much different. However, when the CaO is relatively impure, the whiteness of the precipitated aragonite particles (AR-83) is dramatically higher than the corresponding calcite (BM37), due to the unique effect of the process of the present invention.
2. The whiteness of the precipitated particulate aragonite obtained according to the present process attains top quality, independently of the CaO source.

EXAMPLE 14

Effect of the Active Agent/Process on the Specific Gravity (S.G.) of Precipitated Particulate Calcium Carbonate EXAMPLE 1 was repeated using the aqueous calcium hydroxide slurry of PREPARATION I, except that the concentration of decanoic acid was gradually increased.

(A) Determination of the Specific Gravity (S.G.) of a Product Dried at 120° C.

1. The wet filter cake of the $CaCO_3$ sample was dried for 12 hours at 120° C. to remove all free water.
2. A weighed quantity of the dry $CaCO_3$ sample (Wc)+a weighed quantity of tall oil (Wo) (Density of 0.93 g/cm$^3$) were introduced into a 1 l glass beaker.
3. The mixture was stirred with the Hasiangtal HD-550 Dissolver for 10 minutes, at 4000 rpm (using a saw-blade rotor of d=4.8 cm).
4. The slurry was poured into a 250 ml graduated glass settling column and was sonicated in an ultrasound bath for 20 minutes, until all the trapped bubbles were released.
5. The settling column was then evaluated at 20–22° C. for:
   (a) the volume of the slurry—V
   (b) the total net weight of the slurry—W
   Based on the above measurements, the following was calculated:
(1) from the equation: D=W/V g/cm$^3$, the density of the slurry;
(2) from the equation $$1/D=[Wc(Wo+Wc)]/S.G.+[Wo(Wo+Wc)]/0.93,$$

the S.G. of the $CaCO_3$ sample was calculated.
6. The loose bulk density (B.D.) of the dry powder was measured using a balance and a graduated cylinder.

The Process Set Points—Continuous Mode of Operation:
1. Rotor Speed=4000 rpm (Tip Speed ~10 m/sec.)
2. pH=9.5. 3. Temperature=85° C.
4. Carbon dioxide flow rate=180 L.P.H. (liters/hour).
5. Aqueous calcium hydroxide slurry (of Shfeya) –10 wt. %=~6 L.P.H. (to maintain the preset pH value).
6. Active agent concentration=decanoic acid; 0.5; 1; 2; 5; 2; 1 wt. % based on $CaCO_3$.

The results are as follows

TABLE 13 the results of EXAMPLE 14 (A)

| Test # | Sample Code | Active agent | Dosage (wt. %) | Mineralogical Phase XRD | S.G.[†] g/cm$^3$ | Loose B.D.[†] g/cm$^3$ |
|---|---|---|---|---|---|---|
| 1 | Natural $CaCO_3$ | — | — | Calcite | 2.63 | 0.65 |
| 2 | BM-37* | decanoic acid | 1 | Calcite | 2.54 | 0.37 |
| 3 | C** | N.A. | N.A. | Aragonite | 2.56 | 0.54 |
| 4 | AR-81 | decanoic acid | 0.5 | Aragonite | 2.02 | 0.31 |
| 5 | AR-83 | decanoic acid | 1 | Aragonite | 1.90 | 0.30 |
| 6 | AR-118 | decanoic acid | 2 | Aragonite | 1.75 | 0.25 |
| 7 | AR-119 | decanoic acid | 5*** | Aragonite | 1.67 | 0.29 |
| 8 | AR-135 | nonanoic acid | 1 | Aragonite | 1.88 | 0.31 |
| 9 | AR-120 | decanoic acid | 2^ | Aragonite | 1.72 | 0.23 |

*The sample was taken from the batch mode of operation in - EXAMPLE 3.
**Commercial PCC - Aragonite; of Specialty Minerals Inc. (SMI); Opacarb ® A40.
***5 g of AR-119 were dissolved in a 10% HCl solution. The decanoic acid was extracted with 1,2-dichloroethane. HPLC analysis using a C18 column revealed 4.93% (wt; based on the calcium carbonate) of this acid in the sample.
^50 ppm of phosphoric acid were used in addition to the decanoic acid to increase the aspect ratio of the acicular aragonite.
[†]A dry powder after drying for 12 hours at 120° C.
N.A.—Not available.

Notes:
1. The determination of a specific gravity (S.G.) of particulate precipitated aragonite calcium carbonate of the present invention, in a range below 2.5 g/cm$^3$ (after drying at 120° C. for twelve hours as described above, as well as after ignition of the dried material at 500° C. for eight hours) is actually a most important and most decisive test to consider if the technology that was used is under the domain of the present invention.
2. Only the inclusion of gas (probably, as tiny bubbles or "blisters") in closed pores can account for the dramatic reduction of the S.G. of particulate precipitated aragonite calcium carbonate of the present invention. The L.O.D. and the L.O.I. in the latter tests (c. f. (B) and (C), respectively) do not leave many logical choices to account for this phenomenon. Also, this is in accordance with the facts i. that the product of the present invention is obtained under flotation conditions, and ii. that the high hiding power of the paints, in which the particulate precipitated aragonite calcium carbonate of the present invention was used, are probably due to the high effective refractive index of this product of the present invention, which is much higher than that expected of similar products that are produced according to the prior art (c. f. data collected in EXAMPLE 15 and the comparison made to paint formulations that were based on raw materials of the prior art).
3. The idea of using porous particles, to increase their effective refractive index in coatings, is not new. For instance, Rohm & Haas produces a series of such products, e. g. Ropaque ® OP96 and Ropaque ® OP3000. However, these particles are of an organic polymeric nature of which cost and adaptation to the environment is not to be compared with precipitated calcium carbonate particles.

(B) Determination of the Specific Gravity (S.G.) of a Product Calcined at 300° C.

1. The wet filter cake of the $CaCO_3$ sample was dried for 12 hours at 120° C. to remove all the free water.
2. The weighed dry sample was heated for 8 hours at 300° C. The loss on drying (L.O.D.) was then determined.
3. The S.G. of the heated powder was measured as above (c. f. (A)).
4. The loose bulk density (B.D.) of the dry powder was measured using a balance and a graduated cylinder.

The results are as follows:

TABLE 14 the results of EXAMPLE 14 (B)

| Test # | Sample Code | Active agent | Dosage (wt. %) | L.O.D. wt. % 300° C. | S.G.† g/cm³ | Loose B.D.† g/cm³ |
|---|---|---|---|---|---|---|
| 10 | Natural CaCO₃ | — | — | 0.10 | 2.63 | 0.651 |
| 11 | BM-37* | decanoic acid | 1 | 2.21 | 2.64 | 0.372 |
| 12 | C** | N.A. | N.A. | 1.3 | 2.63 | 0.54 |
| 13 | AR-81 | decanoic acid | 0.5 | 0.83 | 2.19 | 0.255 |
| 14 | AR-83 | decanoic acid | 1 | 0.89 | 2.11 | 0.265 |
| 15 | AR-118 | decanoic acid | 2 | 2.32 | 2.03 | 0.200 |
| 16 | AR-119 | decanoic acid | 5 | 5.73 | 2.01 | 0.200 |
| 17 | AR-135 | nonanoic acid | 1 | 0.95 | 2.12 | 0.238 |
| 18 | AR-120 | decanoic acid | 2^ | 2.27 | 2.02 | 0.235 |

*The sample was taken from the batch mode of operation in-EXAMPLE 3.
**Commercial PCC - Aragonite; of Specialty Minerals Inc. (SMI); Opacarb ® A40.
^ 50 ppm of phosphoric acid were used in addition to the decanoic acid.
†A dry powder after heating for 8 hours at 300° C.
N.A.—Not available.

(C) Determination of the Specific Gravity (S.G.) of a Product Calcined at 500° C.
1. The wet filter cake of the CaCO₃ sample was dried for 12 hours at 120° C. to remove all the free water.
2. The dry sample was calcined for 8 hours at 500° C. The loss on ignition (L.O.I.) was then determined.
3. The S.G. of the calcined powder was measured as above.
4. The loose bulk density (B.D.) of the dry powder was measured using a balance and a graduated cylinder.

The results are as follows:

TABLE 15 the results of EXAMPLE 14 (C)

| Test # | Sample Code | Dosage % (wt) | L.O.I. % (wt) 500° C.^^ | S.G.† g/cm³ | Loose B.D.† g/cm³ |
|---|---|---|---|---|---|
| 19 | Natural CaCO₃ | — | 0.18 | 2.70 | 0.75 |
| 20 | BM-37 | 1* | 2.58 | 2.60 | 0.38 |
| 21 | C** | N.A. | 2.02 | 2.71 | 0.55 |
| 22 | AR-81 | 0.5 | 1.32 | 2.13 | 0.23 |
| 23 | AR-83 | 1 | 1.44 | 2.03 | 0.22 |
| 24 | AR-118 | 2 | 2.07 | 2.01 | 0.18 |
| 25 | AR-119 | 5*** | 5.25 | 1.93 | 0.19 |
| 26 | AR-135 | 1 | 1.44 | 2.01 | 0.24 |
| 27 | AR-120 | 2^ | 2.37 | 1.91 | 0.18 |

*The sample was taken from the batch mode of operaton in-EXAMPLE 3.
**Commercial PCC - Aragonite; of Specialty Minerals Inc. (SMI), Opacarb ® A40.
***5 g of AR-119 were dissolved in a 10% HCl solution. No decanoic acid could be extracted or detected, as is expected of such molecules when they are subjected to heating for 8 hours at 500° C.
^^ 50 ppm of phosphoric acid were used in addition to the decanoic acid.
^ Aragonite is converted into calcite at T > 400° C.
†A dry powder after dying for 12 hours at 120° C. and thereafter heating for 8 hours at 500° C.
N.A.—Not available.

EXAMPLE 15
Preparation of Exterior White Paint—Hercules Inc.

The procedure for the preparation of this paint was obtained from Hercules Inc.; Cellulose & Protein Products D.; Wilmington, Del. 19899 (USA). The procedure followed quite closely the Celanese Resins Formulation No. EP48-222 for the production of this Exterior White Paint (Vinyl Acetate & Acrylate).

(A) The Ingredients used for the 52% PVC Paint and Their Function are as Follows:
1. Tap water.
2. Nopco NDW defoamer.
3. Cellosize QP 15000 thickener (hydroxy ethyl cellulose).
4. Disperse One (45% N.V.) (dispersant).
5. Synperonic NP10 surfactant, wetting agent.
6. Kronos 2160 TiO₂ pigment.
7. Synthetic sodium aluminum silicate (p820) (spacer)
8. Kaolin clay ($D_{50}$=3.1 micron)(spacer)
9. CaCO₃ (spacer)—A GCC product of Polichrom Ltd., Israel
10. Talc ($D_{50}$=12.3 micron)(spacer)
11. PCC—Aragonite of the present invention (samples used contained >80% CaCO₃ in the wet cake products before their drying; no diminution operation took place prior to this use. Namely, the PCC—Aragonite used is not necessarily yet optimized for its purpose).
12. Copolymer vinyl acetate acrylate (55% N.V.) (emulsion)
13. Butyl diglycol acetate solvent (coalescent agent)
14. Kathon LXE preservative.
15. 25% Ammonia (base).
16. Tap water.

Tap water (1), defoamer (2) and thickener (3) were added to a plastic container (d=20 cm; h=30 cm) equipped with a disk (d=8 cm) attached to a Dissolver (Homo Dispers Model HD-550 (0.75 HP) of Hsiangtai Machinery Industry Co. Ltd.; Taiwan). The mixture was stirred at 500 rpm for 5 minutes, after which the dispersant (4) and the wetting agent (5) were added, and stirring was continued at 500 rpm for additional 5 minutes. At this point the stirring speed was increased to 1500 rpm and the respective ingredients for the respective formulations 1–10 were added consecutively, each ingredient over a 5 minute period, according to the order in the above list of reagents (6–16).

The physical properties of the above paints were measured, including the most important property—the hiding power (%) of 90 μm layers of paint were determined with an ACS instrument (Applied Color Systems) and the results are given in the following Tables 16 and 17:

TABLE 16 the result of EXAMPLE 15
Exterior White Paint - Hercules Inc.
Evaluation of the 52% PVC Paints Based on the Precipitated Aragonite Calcium Carbonate Particles of the Present Invention (PCC - Aragonite)

| Raw Material | 1 | 2 | 3 | 4 | 5 | 6 |
|---|---|---|---|---|---|---|
| | % (wt) | | | | | |
| Tap Water | 25.0 | 25.0 | 25.0 | 25.0 | 25.0 | 25.0 |
| Defoamer | 0.1 | 0.1 | 0.1 | 0.1 | 0.1 | 0.1 |
| Thickener (15 K) | 0.3 | 0.3 | 0.3 | 0.3 | 0.3 | 0.3 |
| Dispersant (45%) | 0.9 | 0.9 | 0.9 | 0.9 | 0.9 | 0.9 |
| Wetting Agent | 0.35 | 0.35 | 0.35 | 0.35 | 0.35 | 0.35 |
| TiO₂; Kronos | 14.0 | 9.0 | 9.0 | 9.0 | 9.0 | 8.4 |
| Silicate | 3.7 | 3.7 | 3.7 | 3.7 | 4.0 | 3.9 |
| CaCO₃ - GCC | 7.0 | — | — | — | — | — |
| Kaolin Clay | 6.5 | 6.5 | 6.5 | 6.5 | 10.7 | 6.8 |
| Talc | 6.3 | — | — | — | — | — |
| PCC-Aragonite* | — | 17.75 | 17.75 | 17.75 | 13.00 | 17.75 |
| Copolymer (55%) | 24.5 | 25.5 | 25.5 | 25.5 | 25.4 | 25.4 |

TABLE 16-continued the result of EXAMPLE 15
Exterior White Paint - Hercules Inc.
Evaluation of the 52% PVC Paints Based on the Precipitated
Aragonite Calcium Carbonate Particles of the Present
Invention (PCC - Aragonite)

| | | | | | | |
|---|---|---|---|---|---|---|
| Coalescent Agent | 0.1 | 0.1 | 0.1 | 0.1 | 0.1 | 0.1 |
| Preservative | 0.5 | 0.5 | 0.5 | 0.5 | 0.5 | 0.5 |
| Ammonia | 0.3 | 0.3 | 0.3 | 0.3 | 0.3 | 0.3 |
| Tap Water | 10.45 | 10.0 | 10.0 | 10.0 | 10.35 | 10.2 |
| Total | 100. | 100. | 100. | 100. | 100. | 100. |

The Characteristics of the Paint

| | | | | | | |
|---|---|---|---|---|---|---|
| Solids (%) | 50.98 | 50.98 | 50.98 | 50.98 | 50.67 | 50.82 |
| P.V.C. (%) | 51.77 | 51.32 | 51.32 | 51.32 | 51.51 | 51.55 |
| Hiding Power (%) | 94.0 | 94.4 | 94.9 | 95.5 | 95.1 | 94.9 |
| Viscosity (K.U.) | 92.0 | 92.0 | 93.2 | 98.0 | 100.0 | 98.0 |
| Hegman | 4.5 | 5.5 | 5.5 | 5.0 | 4.0 | 4.5 |
| Bulk Density (g/cm$^3$) | 1.317 | 1.259 | 1.257 | 1.248 | 1.226 | 1.221 |
| Saving of TiO$_2$ (%) | — | 35.7 | 35.7 | 35.7 | 35.7 | 40.0 |
| Weight Saving (%) | — | 4.4 | 4.6 | 5.2 | 6.9 | 7.3 |

| Formulation No. | Pigment* | Sample Code | Active Agent | Active Agent % (wt) |
|---|---|---|---|---|
| 1 | Reference Paint | — | — | — |
| 2 | PCC - Aragonite | AR-81 | Decanoic acid | 0.5 |
| 3 | PCC - Aragonite | AR-83 | Decanoic acid | 1.0 |
| 4 | PCC - Aragonite | AR-118 | Decanoic acid | 2.0 |
| 5 | PCC - Aragonite | AR-119 | Decanoic acid | 5.0 |
| 6 | PCC - Aragonite | AR-118 | Decanoic acid | 2.0 |

TABLE 17 the results of EXAMPLE 15
Exterior White Paint - Hercules Inc.
Evaluation of the 52% PVC Paints Based on the
Precipitated Aragonite Calcium Carbonate Particles of
the Present Invention (PCC - Aragonite)

| Raw Material | 1 | 7 | 8 | 9 | 10 |
|---|---|---|---|---|---|
| | | | % (wt) | | |
| Tap Water | 25.0 | 25.0 | 25.0 | 25.0 | 25.0 |
| Defoamer | 0.1 | 0.1 | 0.1 | 0.1 | 0.1 |
| Thickener (15 K) | 0.3 | 0.3 | 0.3 | 0.3 | 0.3 |
| Dispersant (45%) | 0.9 | 0.9 | 0.9 | 0.9 | 0.9 |
| Wetting Agent | 0.35 | 0.35 | 0.35 | 0.35 | 0.35 |
| TiO$_2$; Kronos | 14.0 | 7.0 | 7.0 | 6.3 | 12.0 |
| Silicate | 3.7 | 4.8 | 4.2 | 4.2 | 3.7 |
| CaCO$_3$ - GCC | 7.0 | — | — | — | — |
| Kaolin Clay | 6.5 | 7.1 | 12.5 | 13.1 | 6.5 |
| Talc | 6.3 | — | — | — | — |
| PCC-Aragonite* | — | 17.75 | 13.0 | 13.0 | 15.3* |
| Copolymer (55%) | 24.5 | 25.5 | 26.0 | 26.0 | 24.5 |
| Coalescent Agent | 0.1 | 0.1 | 0.1 | 0.1 | 0.1 |
| Preservative | 0.5 | 0.5 | 0.5 | 0.5 | 0.5 |
| Ammonia | 0.3 | 0.3 | 0.3 | 0.3 | 0.3 |
| Tap Water | 10.45 | 10.3 | 9.75 | 9.85 | 10.45 |
| Total | 100. | 100. | 100. | 100. | 100. |

The Characteristics of the Paint

| | | | | | |
|---|---|---|---|---|---|
| Solids (%) | 50.98 | 50.98 | 50.98 | 50.98 | 50.98 |
| P.V.C. (%) | 51.77 | 51.32 | 51.32 | 51.32 | 51.91 |
| Hiding Power (%) | 94.0 | 94.2 | 94.3 | 94.0 | 92.7 |
| Viscosity (K.U.) | 92.0 | 96.8 | 98.8 | 98.0 | 90.2 |
| Hegman | 4.5 | 4.5 | 4.5 | 4.5 | 4.5 |
| Bulk Density (g/cm$^3$) | 1.317 | 1.179 | 1.159 | 1.224 | 1.300 |

TABLE 17-continued the results of EXAMPLE 15
Exterior White Paint - Hercules Inc.
Evaluation of the 52% PVC Paints Based on the
Precipitated Aragonite Calcium Carbonate Particles of
the Present Invention (PCC - Aragonite)

| | | | | |
|---|---|---|---|---|
| Saving of TiO$_2$ (%) | — | 50.0 | 50.0 | 55.0 | 14.3 |
| Weight Saving (%) | — | 10.5 | 12.0 | 7.0 | 1.3 |

| Formulation No. | Pigment* | Sample Code | Active Agent | Active Agent % (wt) |
|---|---|---|---|---|
| 1 | Reference Paint | — | — | — |
| 7 | PCC - Aragonite | AR-118 | Decanoic acid | 2.0 |
| 8 | PCC - Aragonite | AR-119 | Decanoic acid | 5.0 |
| 9 | PCC - Aragonite | AR-119 | Decanoic acid | 5.0 |
| 10 | PCC - Aragonite | C** | N.A. | N.A. |

**Commercial PCC - Aragonite; of Specialty Minerals Inc. (SMI); Opac-arb ® A40.

(B) The Ingredients of the 32% PVC Paint and Their Function are as Follows:

1. Tap water. 2. Nopco NDW defoamer.
3. Cellosize QP 15000 thickener (hydroxy ethyl cellulose).
4. Disperse One (45% N.V.) (dispersant).
5. Synperonic NP10 surfactant; wetting agent
6. Kronos 2160 TiO$_2$ pigment. 7. Synthetic Na—Al silicate (p820) (spacer).
8. Kaolin clay (D$_{50}$=3.1 micron)(spacer)
9. CaCO$_3$ (spacer)—a GCC product of Polichrom Ltd., Israel
10. Talc (D$_{50}$=12.3 micron)(spacer)
11. PCC—aragonite of the present invention (samples used contained >80% CaCO$_3$ in the wet cake products before their drying; no diminution operation took place prior to this use. However, the PCC—aragonite used is not necessarily yet optimized for its purpose).
12. Propylene glycol (solvent).
13. Copolymer vinyl acetate acrylate (55% N.V.) (emulsion).
14. Butyl diglycol acetate solvent (coalescent agent).
15. Kathon LXE preservative. 16. 25% Ammonia (base). 17. Tap water.

Tap water (1), defoamer (2) and thickener (3) were added to a plastic container (d=20 cm; h=30 cm) equipped with a disk (d=8 cm) attached to a Dissolver (Homo Dispers Model HD-550 (0.75 HP) of Hsiangtai Machinery Industry Co. Ltd.; Taiwan). The mixture was stirred at 500 rpm for 5 minutes, after which the dispersant (4) and the wetting agent (5) were added, and stirring was continued at 500 rpm for additional 5 minutes. At this point the stirring speed was increased to 1500 rpm and the respective ingredients for the respective formulations 1–10 were added consecutively, each ingredient over a 5 minute period, according to the order in the above list of reagents (6–15).

The physical properties of the above paints were measured, including the most important property—the hiding power (%) of 90 μm layers of paint were determined with an ACS instrument (Applied Color Systems) and the results are given in the following Table 18:

TABLE 18 the results of EXAMPLE 15
Exterior White Paint - Hercules Inc.
Evaluation of the 32% PVC Paints Based on
the Precipitated Aragonite Calcium Carbonate Particles
of the Present Invention (PCC - Aragonite)

| Raw Material | 11 | 12 | 13 | 14 | 15 | 16 |
|---|---|---|---|---|---|---|
| | | | % (wt) | | | |
| Tap Water | 17.8 | 17.8 | 17.8 | 17.8 | 17.8 | 17.8 |
| Defoamer | 0.15 | 0.15 | 0.15 | 0.15 | 0.15 | 0.15 |
| Thickener (15 K) | 0.22 | 0.22 | 0.22 | 0.22 | 0.22 | 0.22 |
| Dispersant (45%) | 0.60 | 0.60 | 0.60 | 0.60 | 0.60 | 0.60 |
| Wetting Agent | 0.34 | 0.34 | 0.34 | 0.34 | 0.34 | 0.34 |
| $TiO_2$; Kronos | 22.5 | 20.0 | 20.0 | 19.0 | 18.0 | 19.0 |
| Silicate | 2.25 | 2.25 | 2.25 | 2.25 | 2.25 | — |
| CaCO3 - GCC | 5.0 | — | — | — | — | — |
| PCC-Aragonite* | — | 7.5 | 7.5 | 8.5 | 9.25 | 13.0 |
| Propylene Glycol | 2.70 | 2.70 | 2.70 | 2.70 | 2.70 | 2.70 |
| Copolymer (55%) | 37.45 | 37.45 | 37.45 | 37.45 | 38.0 | 33.4 |
| Coalescent Agent | 0.18 | 0.18 | 0.18 | 0.18 | 0.18 | 0.18 |
| Preservative | 0.45 | 0.45 | 0.45 | 0.45 | 0.45 | 0.45 |
| Ammonia | 0.30 | 0.30 | 0.30 | 0.30 | 0.30 | 0.30 |
| Tap Water | 10.06 | 10.06 | 10.06 | 10.06 | 9.76 | 11.86 |
| Total | 100. | 100. | 100. | 100. | 100. | 100. |
| The Characteristics of the Paint | | | | | | |
| Solids (%) | 50.35 | 50.35 | 50.35 | 50.35 | 50.35 | 50.37 |
| P.V.C. (%) | 32.59 | 32.64 | 32.64 | 32.93 | 32.64 | 36.73 |
| Hiding Power (%) | 91.0 | 91.4 | 91.4 | 91.0 | 90.8 | 91.0 |
| Viscosity (K.U.) | 87.2 | 98.0 | 97.4 | 96.2 | 87.8 | 90.2 |
| Hegman | 5.5 | 5.5 | 5.5 | 5.5 | 5.0 | 5.5 |
| Bulk Density (g/cm³) | 1.18 | 1.128 | 1.127 | 1.109 | 1.005 | 1.073 |
| Saving of $TiO_2$ (%) | — | 11.1 | 11.1 | 15.5 | 20.0 | 15.5 |
| Weight Saving (%) | — | 4.4 | 4.5 | 6.0 | 14.8 | 6.8 |

| Formulation No. | Pigment* | Sample Code | Active Agent | Active Agent % (wt) |
|---|---|---|---|---|
| 11 | Reference Paint | — | — | — |
| 12 | PCC-Aragonite | AR-118 | Decanoic acid | 2.0 |
| 13 | PCC-Aragonite | AR-119 | Decanaic acid | 5.0 |
| 14 | PCC-Aragonite | AR-119 | Decanoic acid | 5.0 |
| 15 | PCC-Aragonite | AR-119 | Decanoic acid | 5.0 |
| 16 | PCC-Aragonite | AR-118 | Decanoic acid | 2.0 |

Notes:
1. The particulate precipitated aragonite calcium carbonate of the present invention (PCC-Aragonite) can be used to produce paints without a substantial prior size reduction, except that effected by the mixing system of the production of the paint, which is anyway being used in this art to thoroughly disperse the pigments in the various formulations.
2. Though the particulate precipitated aragonite calcium carbonate of the present invention (PCC-Aragonite) is not yet optimized for its use in the production of paints and though the formulations used are by no means optimized, still this product is able to substitute over 50% of the expensive titanium oxide pigment without any deterioration of the resulting paint, as it manifested by the hiding power measured.
3. As the coatings (paints) are being sold and used by volume, and not by weight, the additional saving resulting from using the particulate precipitated aragonite calcium carbonate of the present invention (PCC-Aragonite) can surpass 10% on all the constituents of the coating, including the titanium oxide.
4. For simplicity in formulating the above mentioned paints, dry samples of The particulate precipitated aragonite calcium carbonate of the present invention (PCC-Aragonite), were used. However, wet filter cakes that contain even more water than 20% wt. %, based on wet $CaCO_3$ cake, can be used, provided that this water is being taken in account. However, on an industrial scale, dry PCC-Aragonite will be rarely used, due to the economy of using the wet product.

While the invention has been described with respect to a limited number of embodiments, it will be appreciated that many variations, modifications and other applications of the invention may be made.

What is claimed is:

1. A precipitated aragonite calcium carbonate (PACC) having a specific gravity less than 2.5 g/cm³, when determined by a method that comprises:
   a. drying said PACC for 12 hours at 120° C.;
   b. mixing a weighed quantity ($W_c$) of the dried PACC with a weighed quantity ($W_o$) of tall oil having a density 0.93 g/cm³;
   c. sonicating the mixture in an ultrasound bath for 20 minutes;
   d. measuring the total volume of the mixture (V) and the total weight of the mixture (W) at 20–22° C. and calculating the density D therefrom from the following equation $$D = W/V; \text{ and}$$

e. calculating the specific gravity (S.G.) of the PACC from the following equation:

$$1/D = [W_c(W_o + W_c)]/S.G. + [W_o(W_o + W_c)]/0.93.$$

2. A precipitated aragonite calcium carbonate according to claim 1, wherein the specific gravity is less than 2.3 g/cm³.

3. A precipitated aragonite calcium carbonate according to claim 1, wherein the specific gravity is less than 2.0 g/cm³.

4. A precipitated aragonite calcium carbonate according to claim 1, wherein the specific gravity is less than 1.8 g/cm³.

5. A precipitated aragonite calcium carbonate according to claim 1, having a specific gravity less than 2.5 g/cm³, wherein in the method for determining the specific gravity, the dried PACC is heated for 8 hours at 500° C. before mixing with tall oil.

6. A precipitated aragonite calcium carbonate according to claim 1, comprising at least one carboxylic acid calcium salt, wherein the carboxylic acid is of the formula: $CH_3(CH_2)_nCOOH$, where n is 7, 8 or 9.

7. A precipitated aragonite calcium carbonate according to claim 1, having a crystallographic purity (aragonite/(aragonite+calcite)) of at least 90%.

8. A precipitated aragonite calcium carbonate according to claim 7, wherein the crystallographic purity (aragonite/(aragonite+calcite)) is above 95%.

9. A precipitated aragonite calcium carbonate according to claim 1, having a crystallographic purity (aragonite/(aragonite+calcite)) of less than 90%.

10. A precipitated aragonite calcium carbonate according to claim 6, wherein said at least one carboxylic acid calcium salt is disposed inside crystals of PACC.

11. A precipitated aragonite calcium carbonate according to claim 6, wherein said at least one carboxylic acid calcium salt is present at a concentration within the range of 0.2–10 wt % calculated as carboxylic acid(s) and based on the weight of PACC.

12. A process for producing a precipitated aragonite calcium carbonate (PACC), which comprises reacting a reaction mixture of an aqueous calcium hydroxide slurry, including at least one active agent selected from the group consisting of carboxylic acids of formula $CH_3(CH_2)_n COOH$, where n is 7, 8 or 9, carboxylate salts thereof, esters thereof, anhydrides thereof, acyl halides thereof and ketenes thereof of the formula $CH_3(CH_2)_{n-1}C=C=O$, wherein n is as defined previously, with carbon dioxide or a gas containing carbon dioxide, wherein at least one of the active agent added to the reaction mixture or reaction conditions of temperature, pH, mode of operation and reactant concentrations, are selected to yield precipitated aragonite calcium carbonate with a specific gravity of less than 2.5 g/cm$^3$, when determined by a method that comprises:
  a. drying said PACC for 12 hours at 120° C.;
  b. mixing a weighed quantity ($W_c$) of the dried PACC with a weighed quantity ($W_o$) of tall oil having a density 0.93 g/cm$^3$;
  c. sonicating the mixture in an ultrasound bath for 20 minutes;
  d. measuring the total volume of the mixture (V) and the total weight of the mixture (W) at 20–22° C. and calculating the density D therefrom from the following equation $$D=W/V;\text{ and}$$

e. calculating the specific gravity (S.G.) of the PACC from the following equation:

$$1/D=[W_c(W_o+W_c)]/S.G.+[W_o(W_o+W_c)]/0.93.$$

13. A process according to claim 12, wherein said at least one active agent is selected from the group consisting of carboxylic acids of formula $CH_3(CH_2)_n COOH$, where n is 7, 8 or 9, and carboxylate calcium salts thereof.

14. A process according to claim 12, wherein said at least one active agent has a concentration within the range of 0.2 wt. % and 10 wt. % calculated as carboxylic acid(s) and based on the formed weight of PACC.

15. A process according to claim 14, wherein said concentration of the at least one active agent is within the range of 0.3 wt. % and 5 wt. %, calculated as carboxylic acid(s) and based on the formed weight of PACC.

16. A process according to claim 12, wherein said precipitated aragonite calcium carbonate has a crystallographic purity (aragonite/(aragonite+calcite)) of at least 90%.

17. A process according to claim 16, wherein said crystallographic purity (aragonite/(aragonite+calcite)) is above 95%.

18. A process according to claim 12, wherein said PACC has a crystallographic purity (aragonite/(aragonite+calcite)) of less than 90%.

19. A precipitated aragonite calcium carbonate produced by the process of claim 12.

20. A precipitated aragonite calcium carbonate according to claim 19, wherein, in the method for determining the specific gravity, the dried PACC is heated for 8 hours at 500° C. before mixing with oil.

21. A precipitated aragonite calcium carbonate according to claim 19, having a crystallographic purity (aragonite/(aragonite+calcite)) of at least 90%.

22. A precipitated aragonite calcium carbonate according to claim 21, wherein said crystallographic purity (aragonite/(aragonite+calcite)) is above 95%.

23. A precipitated aragonite calcium carbonate according to claim 19, wherein said PACC has a crystallographic purity (aragonite/(aragonite+calcite)) of less than 90%.

24. A process according to claim 16, wherein:
  said at least one active agent has a concentration within the range between 0.2 wt. % and 10 wt. % calculated as carboxylic acid(s) and based on the weight of calcium carbonate;
  said at least one active agent is added either into the reaction mixture or by pre-mixing with the slurry;
  said slurry contains calcium hydroxide in a concentration within the range of from 3 to 30 wt. %;
  said slurry has a pH range of from 8 to 11; and
  said temperature is in the range between 60° C. and the boiling temperature of the reaction mixture; and
  said process is a continuous or semi-continuous mode of operation.

25. A process according to claim 12, wherein the specific gravity is less than 2.3 g/cm$^3$.

26. A process according to claim 12, wherein the specific gravity is less than 2.0 g/cm$^3$.

27. A process according to claim 12, wherein the specific gravity is less than 1.8 g/cm$^3$.

28. A process according to claim 24, wherein:
  said concentration of the at least one active agent is within the range between 0.3 wt. % and 5 wt. %, calculated as carboxylic acid(s) and based on the weight of calcium carbonate;
  said at least one active agent is added into the reaction mixture;
  said slurry contains a calcium hydroxide in a concentration within the range of from 4 to 20 wt. %;
  said pH is within the range of from 9 to 10;
  said temperature is in the range between 80° C. and the boiling temperature of the reaction mixture; and
  said mode of operation is a continuous mode of operation.

29. A process according to claim 28, wherein:
  said concentration of said at least one active agent is within the range between 0.4 wt. % and 3 wt. %, calculated as carboxylic acid and based on the weight of calcium carbonate;
  said temperature is in the range between 90° C. and the boiling temperature of the reaction mixture; and
  said slurry contains calcium hydroxide in a concentration within the range of from 5 wt. % to 15 wt. %.

30. A process according to claim 12, which is conducted as a flotation process in a flotation cell.

31. A process for producing a precipitated aragonite calcium carbonate (PACC), which comprises reacting in a reaction mixture an aqueous calcium hydroxide slurry with carbon dioxide or a gas containing carbon dioxide, wherein at least one active agent is included in the reaction mixture, each such active agent being selected from the group consisting of carboxylic acids of the formula $CH_3(CH)_n COOH$, wherein n is 7, 8 or 9, and carboxylate salts, acid anhydrides, esters, and acyl halides of said carboxylic acids, and ketenes of the formula $CH_3(CH_2)_{n-1}C=C=O$, wherein n is as defined previously.

32. A process according to claim 31, wherein said at least one active agent has a concentration within the range between 0.2 wt. % and 10 wt. % calculated as carboxylic acid(s) and based on the formed weight of PACC.

33. A process according to claim 32, wherein said concentration of the at least one active agent is within the range between 0.3 wt. % and 5 wt. %, calculated as carboxylic acid(s) and based on the formed weight of PACC.

34. A process according to claim 33, wherein said concentration of said at least one active agent is within the range between 0.4 wt. % and 3 wt. %, calculated as carboxylic acid and based on the formed weight of PACC.

35. A process according to claim 31, wherein said precipitated aragonite calcium carbonate has a crystallographic purity (aragonite/(aragonite+calcite)) of at least 90%.

36. A process according to claim 35, wherein said crystallographic purity (aragonite/(aragonite+calcite)) is above 95%.

37. A process according to claim 31, wherein said PACC has a crystallographic purity (aragonite/(aragonite+calcite)) of less than 90%.

38. A process according to claim 31, wherein said at least one of said active agent and said conditions are selected to yield a specific gravity less than 2.3 g/cm$^3$, when determined by a method that comprises:

a. drying said PACC for 12 hours at 120° C.;
b. mixing a weighed quantity ($W_c$) of the dried PACC with a weighed quantity ($W_o$) of tall oil having a density 0.93 g/cm$^3$;
c. sonicating the mixture in an ultrasound bath for 20 minutes;
d. measuring the total volume of the mixture (V) and the total weight of the mixture (W) at 20–22° C. and calculating the density D therefrom from the following equation $$D=W/V; \text{ and}$$

e. calculating the specific gravity (S.G.) of the PACC from the following equation:

$$1/D=[W_c(W_o+W_c)]/S.G.+[W_o(W_o+W_c)]/0.93.$$

39. A process according to claim 38, wherein said at least one of said active agent and said conditions are selected to yield a specific gravity less than 2.0 g/cm$^3$.

40. A precipitated aragonite calcium carbonate (PACC) produced by the process of claim 31, wherein the specific gravity is less than 2.5 g/cm$^3$, when determined by a method that comprises:

a. drying said PACC for 12 hours at 120° C.;
b. mixing a weighed quantity ($W_c$) of the dried PACC with a weighed quantity ($W_o$) of tall oil having a density 0.93 g/cm$^3$;
c. sonicating the mixture in an ultrasound bath for 20 minutes;
d. measuring the total volume of the mixture (V) and the total weight of the mixture (W) at 20–22° C. and calculating the density D therefrom from the following equation $$D=W/V; \text{ and}$$

e. calculating the specific gravity (S.G.) of the PACC from the following equation:

$$1/D=[W_c(W_o+W_c)]/S.G.+[W_o(W_o+W_c)]/0.93.$$

41. A precipitated aragonite calcium carbonate according to claim 40, wherein, in the method for determining the specific gravity, the dried PACC is heated for 8 hours at 500° C. before mixing with oil.

42. A precipitated aragonite calcium carbonate produced by the process of claim 31.

43. A precipitated aragonite calcium carbonate according to claim 42, having a crystallographic purity (aragonite/(aragonite+calcite)) of at least 90%.

44. A precipitated aragonite calcium carbonate according to claim 43, wherein said crystallographic purity (aragonite/(aragonite+calcite)) is above 95%.

45. A precipitated aragonite calcium carbonate according to claim 31, wherein said PACC has a crystallographic purity (aragonite/(aragonite+calcite)) of less than 90%.

46. A precipitated aragonite calcium carbonate produced by the process of claim 31, wherein said at least one active agent is present inside crystals of PACC as a calcium salt of said carboxylic acid.

47. A precipitated aragonite calcium carbonate according to claim 46, wherein said at least one carboxylic acid calcium salt has a concentration within the range between 0.2 wt. % and 10 wt. % calculated as carboxylic acid(s) and based on the weight of PACC.

48. A process according to claim 35, wherein:

the concentration of the at least one active agent is within the range between 0.2 wt. % and 10 wt. %, calculated as carboxylic acid(s) and based on the weight of calcium carbonate;

said slurry contains calcium hydroxide in a concentration within the range of 3 to 30 wt. %;

said reaction mixture has a pH is within the range of from 8 to 11;

the reaction is carried out at a temperature is in the range between 60° C. and the boiling temperature of the reaction mixture;

said process is carried out under a continuous or a semi-continuous mode of operation; and said at least one active agent is added either into the reaction mixture or by pre-mixing with the slurry.

49. A process according to claim 48, wherein: said concentration of the at least one active agent is within the range between 0.3 wt. % and 5 wt. %, calculated as carboxylic acid(s) and based on the weight of calcium carbonate;

said slurry contains calcium hydroxide in a concentration within the range of from 4 to 20 wt. %;

said pH is within the range of from 9 to 10;

said temperature is in the range between 80° C. and the boiling temperature of the reaction mixture;

said mode of operation is a continuous mode of operation; and said at least one active agent is added into the reaction mixture.

50. A process according to claim 49, wherein:

said concentration of said at least one active agent is within the range between 0.4 wt. % and 3 wt. %, calculated as carboxylic acid and based on the weight of calcium carbonate;

said temperature is in the range between 90° C. and the boiling temperature of the reaction mixture; and said slurry contains calcium hydroxide in a concentration within the range of from 5 to 15 wt. %.

51. A process according to claim 31, wherein said process is conducted as a flotation process in a flotation cell.

* * * * *